United States Patent [19]
Potter

[11] Patent Number: 5,871,750
[45] Date of Patent: *Feb. 16, 1999

[54] LEUKOTOXIN VACCINE COMPOSITIONS AND USES THEREOF

[75] Inventor: Andrew A. Potter, Saskatoon, Canada

[73] Assignee: University Saskatchewan, Saskatoon, Canada

[*] Notice: The term of this patent shall not extend beyond the expiration date of Pat. No. 5,476,657.

[21] Appl. No.: 355,919

[22] Filed: Dec. 14, 1994

Related U.S. Application Data

[63] Continuation of Ser. No. 15,537, Feb. 9, 1993, Pat. No. 5,476,657, which is a continuation of Ser. No. 504,850, Apr. 5, 1990, abandoned, which is a continuation-in-part of Ser. No. 335,018, Apr. 7, 1989, abandoned.

[51] Int. Cl.$^6$ ........................ A61K 39/02; A61K 39/102; C07K 14/285
[52] U.S. Cl. .................................. 424/255.1; 424/184.1; 424/185.1; 424/236.1; 424/832; 530/350; 435/69.1; 435/69.3; 435/71.1
[58] Field of Search ............................ 424/184.1, 185.1, 424/255.1, 236.1; 435/69.3, 69.1, 71.1, 83.2; 530/350

[56] References Cited

U.S. PATENT DOCUMENTS

| | | | |
|---|---|---|---|
| 4,957,739 | 9/1990 | Berget et al. | 424/92 |
| 5,028,423 | 7/1991 | Prickett | 424/85.8 |
| 5,055,400 | 10/1991 | Lo et al. | 435/69.1 |
| 5,165,924 | 11/1992 | Shewen et al. | 424/88 |

FOREIGN PATENT DOCUMENTS

WO 91/15237  10/1991  WIPO .......................... A61K 39/102

OTHER PUBLICATIONS

Gruz et al Mol. Microbiol 4:1933–1940, 1990.
Lally et al J. Dent Res. 68:A913, 1984 Abstract Only.
Shewent et al (1) Vet Med 1078–1083, 1988.
Shewen et al (2) Can J. Res. 30–36, 1988.
Durham et al, Am J. Vet Res 47: 1946–1951 1986.
Biostar Brochure, entitled "3 New Vaccines", released on 6 Jul. 1991.
Baluyut et al., "Interaction of *Pasteurella haemolytica* with Bovine Neutrophils: Identification and Partial Characterization of a Cytotoxin" *Am. J. Vet. Res.* (1981) 42:1920–1926.
Cavalieri et al., "*Escherichia coli* α-hemolysin: Characteristics and probable role in pathogenicity" *Microbiol. Reviews* (1984) 48:326–343.
Conlon et al., "Efficacy of Recombinant Leukotoxin in Protection Against Pneumonic Challenge with Live *Pasteurella haemolytica* A1" *Infect. Immun.* (1991) 59:587–591.
Frey et al., "*Actinobacillus pleuropneumoniae* RTX–toxins: uniform designation of haemolysins, cytolysins, pleurotoxin and their genes" *J. Gen. Microbiol.* (1993) 139:1723–1728.

Gentry et al., "Serum Neutralization of Cytotoxin from *Pasteurella haemolytica*, Serotype 1 and Resistance to Experimental Bovine Pneumonic Pasteurellosis" Vet. *Immunology and Immunopathology* (1985) 9:239–250.
Himmel et al., "Purification and Partial Characterization of a Macrophage Cytotoxin from *Pasteurella haemolytica*" *Am. J. Vet. Res.* (1982) 43:764–767.
Lo et al., "Cloning and Expression of the Leukotoxin Gene of *Pasteurella haemolytica* A1 in *Escherichia coli* K–12" *Infect. Immun.* (1985) 50:667–67.
Lo et al., "Nucleotide Sequence of the Leukotoxin Genes of *Pasteurella haemolytica* A1" *Infect. Immun,* (1987) 55:1987–1996.
Shewen, P.E. and Wilkie, B.N., "Cytotoxin of *Pasteurella haemolytica* Acting on Bovine Leukocytes" *Infect. Immun.* (1982) 35:91–94.
Shewen, P.E. and Wilkie, B.N. "*Pasteurella haemolytica* Cytotoxin: Production by Recognized Serotype and Neutralization by Type–Specific Rabbit Antisera" *Am. J. Vet. Res.* (1983) 44:715–719.
Shewen, P.E. and Wilkie, B.N., "Vaccination of Calves with Leukotoxic Culture Supernatant from *Pasteurella haemolytica*" *Can. J. Vet. Res.* (1988) 52:30–36.
Simpson et al., "Killing of human myelomonocytic leukemia and lymphocytic cell lines by *Actinobacillus actinomycetemocomitans* leukotoxin" *Infect. Immun.* (1988) 56:1162–1166.
Strathdee, C.A. and Lo, R.Y.C., "Extensive Homology between the Leukotoxin of *Pasteurella haemolytica* A1 and the Alpha–Hemolysin of *Escherichia coli*" *Infect. Immun.* (1987) 55:3233–3236.
Sutherland et al., "A Crude Cytotoxin Vaccine Protects Sheep Against Experimental *Pasteurella haemolytica* Serotype A2 Infection" *Vet. Microbiol.* (1989) 19:175–181.
Taichman et al., "Cytopathic effects of Actinobacillus actinomycetemcomitans on monkey blood leukocytes" *J. Peridon. Res.* (1984) 19:133–145.
Welch, R.A., "Pore–forming cytolysins of Gram–negative bacteria" *Mol. Microbiol.* (1991) 5:521–528.
Yates, W.D.G. "A Review of Infectious Bovine Rhinotracheitis, Shipping Fever Pneumonia and Viral–Bacterial Synergism in Respiratory Disease of Cattle" *Can. J. Comp. Med.* (1982) 46:225–263.

*Primary Examiner*—Hazel F. Sidberry
*Attorney, Agent, or Firm*—Robins & Associates

[57] ABSTRACT

New proteins and subunit antigens from *P. haemolytica* for use in stimulating immunity against respiratory diseases such as pneumonia, including shipping fever pneumonia, are disclosed. The subunit antigens include immunogenic amino acid sequences of *P. haemolytica* fimbrial protein, *P. haemolytica* plasmin receptor protein, and *P. haemolytica* 50K outer membrane protein and *P. haemolytica* leukotoxin. The antigens can be used in a vaccine composition, either alone or in combination. Also disclosed are methods of vaccination as well as methods of making the subunit antigens employed in the vaccines.

20 Claims, 18 Drawing Sheets

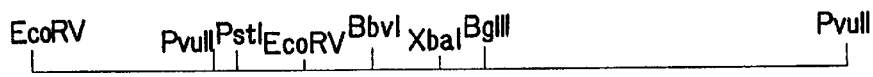
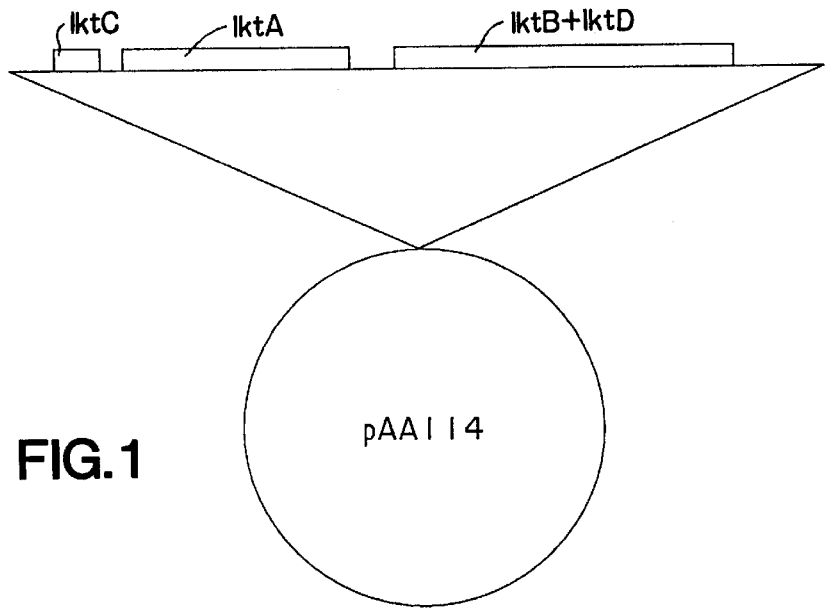
FIG.1
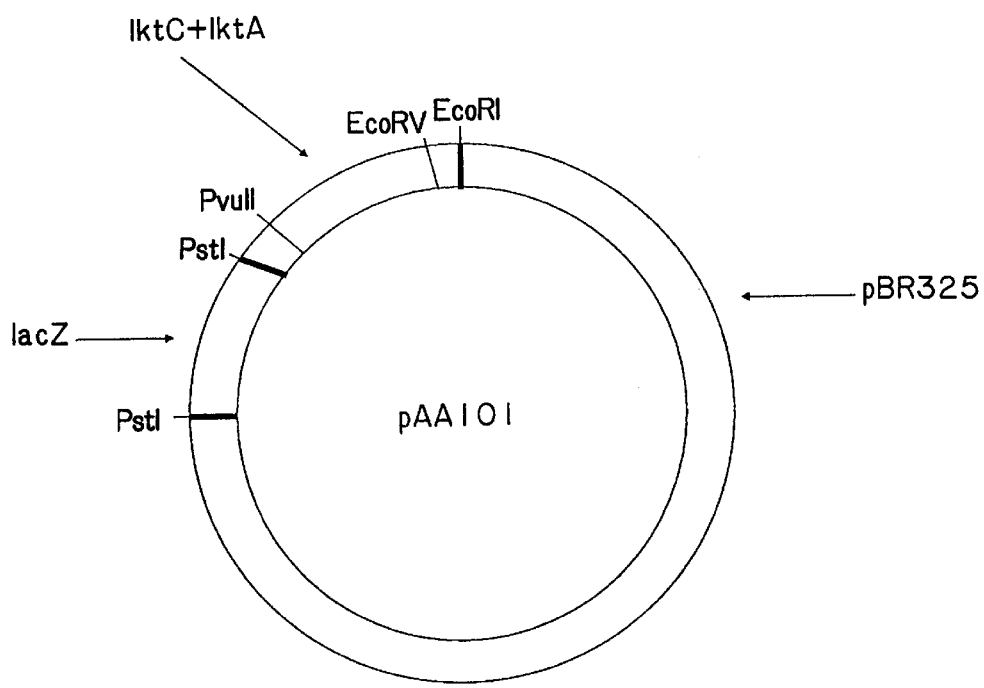
FIG.2

```
   1  MGTRLTTLSNGLKNTLTATKSGLHKAGQSLTQAGSSLKTGAKKIILYIPQNYQYDTEQGN
  61  GLQDLVKAAEELGIEVQREERNNIATAQTSLGTIQTAIGLTERGIVLSAPQIDKLLQKTK
 121  AGQALGSAESIVQNANKAKTVLSGIQSILGSVLAGMDLDEALQNNSNQHALAKAGLELTN
 181  SLIENIANSVKTLDEFGEQISQFGSKLQNIKGLGTLGDKLKNIGGLDKAGLGLDVISGLL
 241  SGATAALVLADKNASTAKKVGAGFELANQVVGNITKAVSSYILAQRVAAGLSSTGPVAAL
 301  IASTVSLAISPLAFAGIADKFNHAKSLESYAERFKKLGYDGDNLLAEYQRGTGTIDASVT
 361  AINTALAAIAGGVSAAAGRRIRGIPGDPVVLQRRDWENPGVTQLNRLAAHPPFASWRNSE
 421  EARTDRPSQQLRSLNGEWRFAWFPAPEAVPESWLECDLPEADTVVVPSNWQMHGYDAPIY
 481  TNVTYPITVNPPFVPTENPTGCYSLTFNVDESWLQEGQTRIIFDGVNSAFHLWCNGRWVG
 541  YGQDSRLPSEFDLSAFLRAGENRLAVMVLRWSDGSYLEDQDMWRMSGIFRDVSLLHKPTT
 601  QISDFHVATRFNDDFSRAVLEAEVQMCGELRDYLRVTVSLWQGETQVASGTAPFGGEIID
 661  ERGGYADRVTLRLNVENPKLWSAEIPNLYRAVVELHTADGTLIEAEACDVGFREVRIENG
 721  LLLLNGKPLLIRGVNRHEHHPLHGQVMDEQTMVQDILLMKQNNFNAVRCSHYPNHPLWYT
 781  LCDRYGLYVVDEANIETHGMVPMNRLTDDPRWLPAMSERVTRMVQRDRNHPSVIIWSLGN
 841  ESGHGANHDALYRWIKSVDPSRPVQYEGGGADTTATDIICPMYARVDEDQPFPAVPKWSI
 901  KKWLSLPGETRPLILCEYAHAMGNSLGGFAKYWQAFRQYPRLQGGFVWDWVDQSLIKYDE
 961  NGNPWSAYGGDFGDTPNDRQFCMNGLVFADRTPHPALTEAKHQQQFFQFRLSGQTIEVTS
1021  EYLFRHSDNELLHWMVALDGKPLASGEVPLDVAPQGKQLIELPELPQPESAGQLWLTVRV
1081  VQPNATAWSEAGHISAWQQWRLAENLSVTLPAASHAIPHLTTSEMDFCIELGNKRWQFNR
1141  QSGFLSQMWIGDKKQLLTPLRDQFTRAPLDNDIGVSEATRIDPNAWVERWKAAGHYQAEA
1201  ALLQCTADTLADAVLITTAHAWQHQGKTLFISRKTYRIDGSGQMAITVDVEVASDTPHPA
1261  RIGLNCQLAQVAERVNWLGLGPQENYPDRLTAACFDRWDLPLSDMYTPYVFPSENGLRCG
1321  TRELNYGPHQWRGDFQFNISRYSQQQLMETSHRHLLHAEEGTWLNIDGFHMGIGGDDSWS
1381  PSVSAEFQLSAGRYHYQLVWCQK
```

FIG.3

```
              10             20             30             40             50             60
         *         *         *         *         *         *         *         *         *         *         *         *
ATG GCT ACT GTT ATA GAT CTA AGC TTC CCA AAA ACT GGG GCA AAA AAA ATT ATC CTC TAT
TAC CGA TGA CAA TAT CTA GAT TCG AAG GGT TTT TGA CCC CGT TTT TTT TAA TAG GAG ATA
Met Ala Thr Val Ile Asp Leu Ser Phe Pro Lys Thr Gly Ala Lys Lys Ile Ile Leu Tyr>
___c___c___c___c___c____RECOMBINANT LEUKOTOXIN PEPTIDE_c___c___c___c___c___c___>
___a___a___VECTOR SEQUENCE_a___a___a__>

70             80             90            100            110            120
         *         *         *         *         *         *         *         *         *         *         *         *
ATT CCC CAA AAT TAC CAA TAT GAT ACT GAA CAA GGT AAT GGT TTA CAG GAT TTA GTC AAA
TAA GGG GTT TTA ATG GTT ATA CTA TGA CTT GTT CCA TTA CCA AAT GTC CTA AAT CAG TTT
Ile Pro Gln Asn Tyr Gln Tyr Asp Thr Glu Gln Gly Asn Gly Leu Gln Asp Leu Val Lys>
___c___c___c___c___c____RECOMBINANT LEUKOTOXIN PEPTIDE_c___c___c___c___c___c___>

130            140            150            160            170            180
         *         *         *         *         *         *         *         *         *         *         *         *
GCG GCC GAA GAG TTG GGG ATT GAG GTA CAA AGA GAA GAA CGC AAT AAT ATT GCA ACA GCT
CGC CGG CTT CTC AAC CCC TAA CTC CAT GTT TCT CTT CTT GCG TTA TTA TAA CGT TGT CGA
Ala Ala Glu Glu Leu Gly Ile Glu Val Gln Arg Glu Glu Arg Asn Asn Ile Ala Thr Ala>
___c___c___c___c___c____RECOMBINANT LEUKOTOXIN PEPTIDE_c___c___c___c___c___c___>

190            200            210            220            230            240
         *         *         *         *         *         *         *         *         *         *         *         *
CAA ACC AGT TTA GGC ACG ATT CAA ACC GCT ATT GGC TTA ACT GAG CGT GGC ATT GTG TTA
GTT TGG TCA AAT CCG TGC TAA GTT TGG CGA TAA CCG AAT TGA CTC GCA CCG TAA CAC AAT
Gln Thr Ser Leu Gly Thr Ile Gln Thr Ala Ile Gly Leu Thr Glu Arg Gly Ile Val Leu>
___c___c___c___c___c____RECOMBINANT LEUKOTOXIN PEPTIDE_c___c___c___c___c___c___>

250            260            270            280            290            300
         *         *         *         *         *         *         *         *         *         *         *         *
TCC GCT CCA CAA ATT GAT AAA TTG CTA CAG AAA ACT AAA GCA GGC CAA GCA TTA GGT TCT
AGG CGA GGT GTT TAA CTA TTT AAC GAT GTC TTT TGA TTT CGT CCG GTT CGT AAT CCA AGA
Ser Ala Pro Gln Ile Asp Lys Leu Leu Gln Lys Thr Lys Ala Gly Gln Ala Leu Gly Ser>
___c___c___c___c___c____RECOMBINANT LEUKOTOXIN PEPTIDE_c___c___c___c___c___c___>

310            320            330            340            350            360
         *         *         *         *         *         *         *         *         *         *         *         *
GCC GAA AGC ATT GTA CAA AAT GCA AAT AAA GCC AAA ACT GTA TTA TCT GGC ATT CAA TCT
CGG CTT TCG TAA CAT GTT TTA CGT TTA TTT CGG TTT TGA CAT AAT AGA CCG TAA GTT AGA
Ala Glu Ser Ile Val Gln Asn Ala Asn Lys Ala Lys Thr Val Leu Ser Gly Ile Gln Ser>
___c___c___c___c___c____RECOMBINANT LEUKOTOXIN PEPTIDE_c___c___c___c___c___c___>

370            380            390            400            410            420
         *         *         *         *         *         *         *         *         *         *         *         *
ATT TTA GGC TCA GTA TTG GCT GGA ATG GAT TTA GAT GAG GCC TTA CAG AAT AAC AGC AAC
TAA AAT CCG AGT CAT AAC CGA CCT TAC CTA AAT CTA CTC CGG AAT GTC TTA TTG TCG TTG
Ile Leu Gly Ser Val Leu Ala Gly Met Asp Leu Asp Glu Ala Leu Gln Asn Asn Ser Asn>
___c___c___c___c___c____RECOMBINANT LEUKOTOXIN PEPTIDE_c___c___c___c___c___c___>

430            440            450            460            470            480
         *         *         *         *         *         *         *         *         *         *         *         *
CAA CAT GCT CTT GCT AAA GCT GGC TTG GAG CTA ACA AAT TCA TTA ATT GAA AAT ATT GCT
GTT GTA CGA GAA CGA TTT CGA CCG AAC CTC GAT TGT TTA AGT AAT TAA CTT TTA TAA CGA
Gln His Ala Leu Ala Lys Ala Gly Leu Glu Leu Thr Asn Ser Leu Ile Glu Asn Ile Ala>
___c___c___c___c___c____RECOMBINANT LEUKOTOXIN PEPTIDE_c___c___c___c___c___c___>
```

FIG.5A

```
                 490         500         510         520         530         540
          *       *   *       *   *       *   *       *   *       *   *       *
        AAT TCA GTA AAA ACA CTT GAC GAA TTT GGT GAG CAA ATT AGT CAA TTT GGT TCA AAA CTA
        TTA AGT CAT TTT TGT GAA CTG CTT AAA CCA CTC GTT TAA TCA GTT AAA CCA AGT TTT GAT
        Asn Ser Val Lys Thr Leu Asp Glu Phe Gly Glu Gln Ile Ser Gln Phe Gly Ser Lys Leu>
        ___c___c___c___c___c___RECOMBINANT LEUKOTOXIN PEPTIDE_c___c___c___c___c___c___>

550         560         570         580         590         600
          *       *   *       *   *       *   *       *   *       *   *       *
        CAA AAT ATC AAA GGC TTA GGG ACT TTA GGA GAC AAA CTC AAA AAT ATC GGT GGA CTT GAT
        GTT TTA TAG TTT CCG AAT CCC TGA AAT CCT CTG TTT GAG TTT TTA TAG CCA CCT GAA CTA
        Gln Asn Ile Lys Gly Leu Gly Thr Leu Gly Asp Lys Leu Lys Asn Ile Gly Gly Leu Asp>
        ___c___c___c___c___c___RECOMBINANT LEUKOTOXIN PEPTIDE_c___c___c___c___c___c___>

610         620         630         640         650         660
          *       *   *       *   *       *   *       *   *       *   *       *
        AAA GCT GGC CTT GGT TTA GAT GTT ATC TCA GGG CTA TTA TCG GGC GCA ACA GCT GCA CTT
        TTT CGA CCG GAA CCA AAT CTA CAA TAG AGT CCC GAT AAT AGC CCG CGT TGT CGA CGT GAA
        Lys Ala Gly Leu Gly Leu Asp Val Ile Ser Gly Leu Leu Ser Gly Ala Thr Ala Ala Leu>
        ___c___c___c___c___c___RECOMBINANT LEUKOTOXIN PEPTIDE_c___c___c___c___c___c___>

670         680         690         700         710         720
          *       *   *       *   *       *   *       *   *       *   *       *
        GTA CTT GCA GAT AAA AAT GCT TCA ACA GCT AAA AAA GTG GGT GCG GGT TTT GAA TTG GCA
        CAT GAA CGT CTA TTT TTA CGA AGT TGT CGA TTT TTT CAC CCA CGC CCA AAA CTT AAC CGT
        Val Leu Ala Asp Lys Asn Ala Ser Thr Ala Lys Lys Val Gly Ala Gly Phe Glu Leu Ala>
        ___c___c___c___c___c___RECOMBINANT LEUKOTOXIN PEPTIDE_c___c___c___c___c___c___>

730         740         750         760         770         780
          *       *   *       *   *       *   *       *   *       *   *       *
        AAC CAA GTT GTT GGT AAT ATT ACC AAA GCC GTT TCT TCT TAC ATT TTA GCC CAA CGT GTT
        TTG GTT CAA CAA CCA TTA TAA TGG TTT CGG CAA AGA AGA ATG TAA AAT CGG GTT GCA CAA
        Asn Gln Val Val Gly Asn Ile Thr Lys Ala Val Ser Ser Tyr Ile Leu Ala Gln Arg Val>
        ___c___c___c___c___c___RECOMBINANT LEUKOTOXIN PEPTIDE_c___c___c___c___c___c___>

790         800         810         820         830         840
          *       *   *       *   *       *   *       *   *       *   *       *
        GCA GCA GGT TTA TCT TCA ACT GGG CCT GTG GCT GCT TTA ATT GCT TCT ACT GTT TCT CTT
        CGT CGT CCA AAT AGA AGT TGA CCC GGA CAC CGA CGA AAT TAA CGA AGA TGA CAA AGA GAA
        Ala Ala Gly Leu Ser Ser Thr Gly Pro Val Ala Ala Leu Ile Ala Ser Thr Val Ser Leu>
        ___c___c___c___c___c___RECOMBINANT LEUKOTOXIN PEPTIDE_c___c___c___c___c___c___>

850         860         870         880         890         900
          *       *   *       *   *       *   *       *   *       *   *       *
        GCG ATT AGC CCA TTA GCA TTT GCC GGT ATT GCC GAT AAA TTT AAT CAT GCA AAA AGT TTA
        CGC TAA TCG GGT AAT CGT AAA CGG CCA TAA CGG CTA TTT AAA TTA GTA CGT TTT TCA AAT
        Ala Ile Ser Pro Leu Ala Phe Ala Gly Ile Ala Asp Lys Phe Asn His Ala Lys Ser Leu>
        ___c___c___c___c___c___RECOMBINANT LEUKOTOXIN PEPTIDE_c___c___c___c___c___c___>

910         920         930         940         950         960
          *       *   *       *   *       *   *       *   *       *   *       *
        GAG AGT TAT GCC GAA CGC TTT AAA AAA TTA GGC TAT GAC GGA GAT AAT TTA TTA GCA GAA
        CTC TCA ATA CGG CTT GCG AAA TTT TTT AAT CCG ATA CTG CCT CTA TTA AAT AAT CGT CTT
        Glu Ser Tyr Ala Glu Arg Phe Lys Lys Leu Gly Tyr Asp Gly Asp Asn Leu Leu Ala Glu>
        ___c___c___c___c___c___RECOMBINANT LEUKOTOXIN PEPTIDE_c___c___c___c___c___c___>
```

FIG.5B

```
            970          980          990         1000         1010         1020
         *    *       *    *       *    *       *    *       *    *       *    *
    TAT CAG CGG GGA ACA GGG ACT ATT GAT GCA TCG GTT ACT GCA ATT AAT ACC GCA TTG GCC
    ATA GTC GCC CCT TGT CCC TGA TAA CTA CGT AGC CAA TGA CGT TAA TTA TGG CGT AAC CGG
    Tyr Gln Arg Gly Thr Gly Thr Ile Asp Ala Ser Val Thr Ala Ile Asn Thr Ala Leu Ala>
    ___c___c___c___c___c____RECOMBINANT LEUKOTOXIN PEPTIDE_c___c___c___c___c___c___>

1030         1040         1050         1060         1070         1080
         *    *       *    *       *    *       *    *       *    *       *    *
    GCT ATT GCT GGT GGT GTG TCT GCT GCT GCA GCC GGC TCG GTT ATT GCT TCA CCG ATT GCC
    CGA TAA CGA CCA CCA CAC AGA CGA CGA CGT CGG CCG AGC CAA TAA CGA AGT GGC TAA CGG
    Ala Ile Ala Gly Gly Val Ser Ala Ala Ala Ala Gly Ser Val Ile Ala Ser Pro Ile Ala>
    ___c___c___c___c___c____RECOMBINANT LEUKOTOXIN PEPTIDE_c___c___c___c___c___c___>

1090         1100         1110         1120         1130         1140
         *    *       *    *       *    *       *    *       *    *       *    *
    TTA TTA GTA TCT GGG ATT ACC GGT GTA ATT TCT ACG ATT CTG CAA TAT TCT AAA CAA GCA
    AAT AAT CAT AGA CCC TAA TGG CCA CAT TAA AGA TGC TAA GAC GTT ATA AGA TTT GTT CGT
    Leu Leu Val Ser Gly Ile Thr Gly Val Ile Ser Thr Ile Leu Gln Tyr Ser Lys Gln Ala>
    ___c___c___c___c___c____RECOMBINANT LEUKOTOXIN PEPTIDE_c___c___c___c___c___c___>

1150         1160         1170         1180         1190         1200
         *    *       *    *       *    *       *    *       *    *       *    *
    ATG TTT GAG CAC GTT GCA AAT AAA ATT CAT AAC AAA ATT GTA GAA TGG GAA AAA AAT AAT
    TAC AAA CTC GTG CAA CGT TTA TTT TAA GTA TTG TTT TAA CAT CTT ACC CTT TTT TTA TTA
    Met Phe Glu His Val Ala Asn Lys Ile His Asn Lys Ile Val Glu Trp Glu Lys Asn Asn>
    ___c___c___c___c___c____RECOMBINANT LEUKOTOXIN PEPTIDE_c___c___c___c___c___c___>

1210         1220         1230         1240         1250         1260
         *    *       *    *       *    *       *    *       *    *       *    *
    CAC GGT AAG AAC TAC TTT GAA AAT GGT TAC GAT GCC CGT TAT CTT GCG AAT TTA CAA GAT
    GTG CCA TTC TTG ATG AAA CTT TTA CCA ATG CTA CGG GCA ATA GAA CGC TTA AAT GTT CTA
    His Gly Lys Asn Tyr Phe Glu Asn Gly Tyr Asp Ala Arg Tyr Leu Ala Asn Leu Gln Asp>
    ___c___c___c___c___c____RECOMBINANT LEUKOTOXIN PEPTIDE_c___c___c___c___c___c___>

1270         1280         1290         1300         1310         1320
         *    *       *    *       *    *       *    *       *    *       *    *
    AAT ATG AAA TTC TTA CTG AAC TTA AAC AAA GAG TTA CAG GCA GAA CGT GTC ATC GCT ATT
    TTA TAC TTT AAG AAT GAC TTG AAT TTG TTT CTC AAT GTC CGT CTT GCA CAG TAG CGA TAA
    Asn Met Lys Phe Leu Leu Asn Leu Asn Lys Glu Leu Gln Ala Glu Arg Val Ile Ala Ile>
    ___c___c___c___c___c____RECOMBINANT LEUKOTOXIN PEPTIDE_c___c___c___c___c___c___>

1330         1340         1350         1360         1370         1380
         *    *       *    *       *    *       *    *       *    *       *    *
    ACT CAG CAG CAA TGG GAT AAC AAC ATT GGT GAT TTA GCT GGT ATT AGC CGT TTA GGT GAA
    TGA GTC GTC GTT ACC CTA TTG TTG TAA CCA CTA AAT CGA CCA TAA TCG GCA AAT CCA CTT
    Thr Gln Gln Gln Trp Asp Asn Asn Ile Gly Asp Leu Ala Gly Ile Ser Arg Leu Gly Glu>
    ___c___c___c___c___c____RECOMBINANT LEUKOTOXIN PEPTIDE_c___c___c___c___c___c___>

1390         1400         1410         1420         1430         1440
         *    *       *    *       *    *       *    *       *    *       *    *
    AAA GTC CTT AGT GGT AAA GCC TAT GTG GAT GCG TTT GAA GAA GGC AAA CAC ATT AAA GCC
    TTT CAG GAA TCA CCA TTT CGG ATA CAC CTA CGC AAA CTT CTT CCG TTT GTG TAA TTT CGG
    Lys Val Leu Ser Gly Lys Ala Tyr Val Asp Ala Phe Glu Glu Gly Lys His Ile Lys Ala>
    ___c___c___c___c___c____RECOMBINANT LEUKOTOXIN PEPTIDE_c___c___c___c___c___c___>
```

FIG.5C

```
              1450          1460          1470          1480          1490          1500
          *     *       *     *       *     *       *     *       *     *       *     *
        GAT AAA TTA GTA CAG TTG GAT TCG GCA AAC GGT ATT ATT GAT GTG AGT AAT TCG GGT AAA
        CTA TTT AAT CAT GTC AAC CTA AGC CGT TTG CCA TAA TAA CTA CAC TCA TTA AGC CCA TTT
        Asp Lys Leu Val Gln Leu Asp Ser Ala Asn Gly Ile Ile Asp Val Ser Asn Ser Gly Lys>

1510          1520          1530          1540          1550          1560
          *     *       *     *       *     *       *     *       *     *       *     *
        GCG AAA ACT CAG CAT ATC TTA TTC AGA ACG CCA TTA TTG ACG CCG GGA ACA GAG CAT CGT
        CGC TTT TGA GTC GTA TAG AAT AAG TCT TGC GGT AAT AAC TGC GGC CCT TGT CTC GTA GCA
        Ala Lys Thr Gln His Ile Leu Phe Arg Thr Pro Leu Leu Thr Pro Gly Thr Glu His Arg>
        ___c___c___c___c___c___RECOMBINANT LEUKOTOXIN PEPTIDE_c___c___c___c___c___c___>

1570          1580          1590          1600          1610          1620
          *     *       *     *       *     *       *     *       *     *       *     *
        GAA CGC GTA CAA ACA GGT AAA TAT GAA TAT ATT ACC AAG CTC AAT ATT AAC CGT GTA GAT
        CTT GCG CAT GTT TGT CCA TTT ATA CTT ATA TAA TGG TTC GAG TTA TAA TTG GCA CAT CTA
        Glu Arg Val Gln Thr Gly Lys Tyr Glu Tyr Ile Thr Lys Leu Asn Ile Asn Arg Val Asp>
        ___c___c___c___c___c___RECOMBINANT LEUKOTOXIN PEPTIDE_c___c___c___c___c___c___>

1630          1640          1650          1660          1670          1680
          *     *       *     *       *     *       *     *       *     *       *     *
        AGC TGG AAA ATT ACA GAT GGT GCA GCA AGT TCT ACC TTT GAT TTA ACT AAC GTT GTT CAG
        TCG ACC TTT TAA TGT CTA CCA CGT CGT TCA AGA TGG AAA CTA AAT TGA TTG CAA CAA GTC
        Ser Trp Lys Ile Thr Asp Gly Ala Ala Ser Ser Thr Phe Asp Leu Thr Asn Val Val Gln>
        ___c___c___c___c___c___RECOMBINANT LEUKOTOXIN PEPTIDE_c___c___c___c___c___c___>

1690          1700          1710          1720          1730          1740
          *     *       *     *       *     *       *     *       *     *       *     *
        CGT ATT GGT ATT GAA TTA GAC AAT GCT GGA AAT GTA ACT AAA ACC AAA GAA ACA AAA ATT
        GCA TAA CCA TAA CTT AAT CTG TTA CGA CCT TTA CAT TGA TTT TGG TTT CTT TGT TTT TAA
        Arg Ile Gly Ile Glu Leu Asp Asn Ala Gly Asn Val Thr Lys Thr Lys Glu Thr Lys Ile>
        ___c___c___c___c___c___RECOMBINANT LEUKOTOXIN PEPTIDE_c___c___c___c___c___c___>

1750          1760          1770          1780          1790          1800
          *     *       *     *       *     *       *     *       *     *       *     *
        ATT GCC AAA CTT GGT GAA GGT GAT GAC AAC GTA TTT GTT GGT TCT GGT ACG ACG GAA ATT
        TAA CGG TTT GAA CCA CTT CCA CTA CTG TTG CAT AAA CAA CCA AGA CCA TGC TGC CTT TAA
        Ile Ala Lys Leu Gly Glu Gly Asp Asp Asn Val Phe Val Gly Ser Gly Thr Thr Glu Ile>
        ___c___c___c___c___c___RECOMBINANT LEUKOTOXIN PEPTIDE_c___c___c___c___c___c___>

1810          1820          1830          1840          1850          1860
          *     *       *     *       *     *       *     *       *     *       *     *
        GAT GGC GGT GAA GGT TAC GAC CGA GTT CAC TAT AGC CGT GGA AAC TAT GGT GCT TTA ACT
        CTA CCG CCA CTT CCA ATG CTG GCT CAA GTG ATA TCG GCA CCT TTG ATA CCA CGA AAT TGA
        Asp Gly Gly Glu Gly Tyr Asp Arg Val His Tyr Ser Arg Gly Asn Tyr Gly Ala Leu Thr>
        ___c___c___c___c___c___RECOMBINANT LEUKOTOXIN PEPTIDE_c___c___c___c___c___c___>

1870          1880          1890          1900          1910          1920
          *     *       *     *       *     *       *     *       *     *       *     *
        ATT GAT GCA ACC AAA GAG ACC GAG CAA GGT AGT TAT ACC GTA AAT CGT TTC GTA GAA ACC
        TAA CTA CGT TGG TTT CTC TGG CTC GTT CCA TCA ATA TGG CAT TTA GCA AAG CAT CTT TGG
        Ile Asp Ala Thr Lys Glu Thr Glu Gln Gly Ser Tyr Thr Val Asn Arg Phe Val Glu Thr>
        ___c___c___c___c___c___RECOMBINANT LEUKOTOXIN PEPTIDE_c___c___c___c___c___c___>
```

FIG.5D

```
            1930         1940         1950         1960         1970         1980
          *       *    *       *    *       *    *       *    *       *    *       *
       GGT AAA GCA CTA CAC GAA GTG ACT TCA ACC CAT ACC GCA TTA GTG GGC AAC CGT GAA GAA
       CCA TTT CGT GAT GTG CTT CAC TGA AGT TGG GTA TGG CGT AAT CAC CCG TTG GCA CTT CTT
       Gly Lys Ala Leu His Glu Val Thr Ser Thr His Thr Ala Leu Val Gly Asn Arg Glu Glu>
       ___c___c___c___c___c____RECOMBINANT LEUKOTOXIN PEPTIDE_c___c___c___c___c___c___>

1990         2000         2010         2020         2030         2040
          *       *    *       *    *       *    *       *    *       *    *       *
       AAA ATA GAA TAT CGT CAT AGC AAT AAC CAG CAC CAT GCC GGT TAT TAC ACC AAA GAT ACC
       TTT TAT CTT ATA GCA GTA TCG TTA TTG GTC GTG GTA CGG CCA ATA ATG TGG TTT CTA TGG
       Lys Ile Glu Tyr Arg His Ser Asn Asn Gln His His Ala Gly Tyr Tyr Thr Lys Asp Thr>
       ___c___c___c___c___c____RECOMBINANT LEUKOTOXIN PEPTIDE_c___c___c___c___c___c___>

2050         2060         2070         2080         2090         2100
          *       *    *       *    *       *    *       *    *       *    *       *
       TTG AAA GCT GTT GAA GAA ATT ATC GGT ACA TCA CAT AAC GAT ATC TTT AAA GGT AGT AAG
       AAC TTT CGA CAA CTT CTT TAA TAG CCA TGT AGT GTA TTG CTA TAG AAA TTT CCA TCA TTC
       Leu Lys Ala Val Glu Glu Ile Ile Gly Thr Ser His Asn Asp Ile Phe Lys Gly Ser Lys>
       ___c___c___c___c___c____RECOMBINANT LEUKOTOXIN PEPTIDE_c___c___c___c___c___c___>

2110         2120         2130         2140         2150         2160
          *       *    *       *    *       *    *       *    *       *    *       *
       TTC AAT GAT GCC TTT AAC GGT GGT GAT GGT GTC GAT ACT ATT GAC GGT AAC GAC GGC AAT
       AAG TTA CTA CGG AAA TTG CCA CCA CTA CCA CAG CTA TGA TAA CTG CCA TTG CTG CCG TTA
       Phe Asn Asp Ala Phe Asn Gly Gly Asp Gly Val Asp Thr Ile Asp Gly Asn Asp Gly Asn>
       ___c___c___c___c___c____RECOMBINANT LEUKOTOXIN PEPTIDE_c___c___c___c___c___c___>

2170         2180         2190         2200         2210         2220
          *       *    *       *    *       *    *       *    *       *    *       *
       GAC CGC TTA TTT GGT GGT AAA GGC GAT GAT ATT CTC GAT GGT GGA AAT GGT GAT GAT TTT
       CTG GCG AAT AAA CCA CCA TTT CCG CTA CTA TAA GAG CTA CCA CCT TTA CCA CTA CTA AAA
       Asp Arg Leu Phe Gly Gly Lys Gly Asp Asp Ile Leu Asp Gly Gly Asn Gly Asp Asp Phe>
       ___c___c___c___c___c____RECOMBINANT LEUKOTOXIN PEPTIDE_c___c___c___c___c___c___>

2230         2240         2250         2260         2270         2280
          *       *    *       *    *       *    *       *    *       *    *       *
       ATC GAT GGC GGT AAA GGC AAC GAC CTA TTA CAC GGT GGC AAG GGC GAT GAT ATT TTC GTT
       TAG CTA CCG CCA TTT CCG TTG CTG GAT AAT GTG CCA CCG TTC CCG CTA CTA TAA AAG CAA
       Ile Asp Gly Gly Lys Gly Asn Asp Leu Leu His Gly Gly Lys Gly Asp Asp Ile Phe Val>
       ___c___c___c___c___c____RECOMBINANT LEUKOTOXIN PEPTIDE_c___c___c___c___c___c___>

2290         2300         2310         2320         2330         2340
          *       *    *       *    *       *    *       *    *       *    *       *
       CAC CGT AAA GGC GAT GGT AAT GAT ATT ATT ACC GAT TCT GAC GGC AAT GAT AAA TTA TCA
       GTG GCA TTT CCG CTA CCA TTA CTA TAA TAA TGG CTA AGA CTG CCG TTA CTA TTT AAT AGT
       His Arg Lys Gly Asp Gly Asn Asp Ile Ile Thr Asp Ser Asp Gly Asn Asp Lys Leu Ser>
       ___c___c___c___c___c____RECOMBINANT LEUKOTOXIN PEPTIDE_c___c___c___c___c___c___>

2350         2360         2370         2380         2390         2400
          *       *    *       *    *       *    *       *    *       *    *       *
       TTC TCT GAT TCG AAC TTA AAA GAT TTA ACA TTT GAA AAA GTT AAA CAT AAT CTT GTC ATC
       AAG AGA CTA AGC TTG AAT TTT CTA AAT TGT AAA CTT TTT CAA TTT GTA TTA GAA CAG TAG
       Phe Ser Asp Ser Asn Leu Lys Asp Leu Thr Phe Glu Lys Val Lys His Asn Leu Val Ile>
       ___c___c___c___c___c____RECOMBINANT LEUKOTOXIN PEPTIDE_c___c___c___c___c___c___>
```

FIG.5E

```
              2410        2420        2430        2440        2450        2460
           *     *     *     *     *     *     *     *     *     *     *     *
        ACG AAT AGC AAA AAA GAG AAA GTG ACC ATT CAA AAC TGG TTC CGA GAG GCT GAT TTT GCT
        TGC TTA TCG TTT TTT CTC TTT CAC TGG TAA GTT TTG ACC AAG GCT CTC CGA CTA AAA CGA
        Thr Asn Ser Lys Lys Glu Lys Val Thr Ile Gln Asn Trp Phe Arg Glu Ala Asp Phe Ala>
        ___c___c___c___c___c_____RECOMBINANT LEUKOTOXIN PEPTIDE_c___c___c___c___c___c___>

2470        2480        2490        2500        2510        2520
           *     *     *     *     *     *     *     *     *     *     *     *
        AAA GAA GTG CCT AAT TAT AAA GCA ACT AAA GAT GAG AAA ATC GAA GAA ATC ATC GGT CAA
        TTT CTT CAC GGA TTA ATA TTT CGT TGA TTT CTA CTC TTT TAG CTT CTT TAG TAG CCA GTT
        Lys Glu Val Pro Asn Tyr Lys Ala Thr Lys Asp Glu Lys Ile Glu Glu Ile Ile Gly Gln>
        ___c___c___c___c___c_____RECOMBINANT LEUKOTOXIN PEPTIDE_c___c___c___c___c___c___>

2530        2540        2550        2560        2570        2580
           *     *     *     *     *     *     *     *     *     *     *     *
        AAT GGC GAG CGG ATC ACC TCA AAG CAA GTT GAT GAT CTT ATC GCA AAA GGT AAC GGC AAA
        TTA CCG CTC GCC TAG TGG AGT TTC GTT CAA CTA CTA GAA TAG CGT TTT CCA TTG CCG TTT
        Asn Gly Glu Arg Ile Thr Ser Lys Gln Val Asp Asp Leu Ile Ala Lys Gly Asn Gly Lys>
        ___c___c___c___c___c_____RECOMBINANT LEUKOTOXIN PEPTIDE_c___c___c___c___c___c___>

2590        2600        2610        2620        2630        2640
           *     *     *     *     *     *     *     *     *     *     *     *
        ATT ACC CAA GAT GAG CTA TCA AAA GTT GTT GAT AAC TAT GAA TTG CTC AAA CAT AGC AAA
        TAA TGG GTT CTA CTC GAT AGT TTT CAA CAA CTA TTG ATA CTT AAC GAG TTT GTA TCG TTT
        Ile Thr Gln Asp Glu Leu Ser Lys Val Val Asp Asn Tyr Glu Leu Leu Lys His Ser Lys>
        ___c___c___c___c___c_____RECOMBINANT LEUKOTOXIN PEPTIDE_c___c___c___c___c___c___>

2650        2660        2670        2680        2690        2700
           *     *     *     *     *     *     *     *     *     *     *     *
        AAT GTG ACA AAC AGC TTA GAT AAG TTA ATC TCA TCT GTA AGT GCA TTT ACC TCG TCT AAT
        TTA CAC TGT TTG TCG AAT CTA TTC AAT TAG AGT AGA CAT TCA CGT AAA TGG AGC AGA TTA
        Asn Val Thr Asn Ser Leu Asp Lys Leu Ile Ser Ser Val Ser Ala Phe Thr Ser Ser Asn>
        ___c___c___c___c___c_____RECOMBINANT LEUKOTOXIN PEPTIDE_c___c___c___c___c___c___>

2710        2720        2730        2740        2750        2760
           *     *     *     *     *     *     *     *     *     *     *     *
        GAT TCG AGA AAT GTA TTA GTG GCT CCA ACT TCA ATG TTG GAT CAA AGT TTA TCT TCT CTT
        CTA AGC TCT TTA CAT AAT CAC CGA GGT TGA AGT TAC AAC CTA GTT TCA AAT AGA AGA GAA
        Asp Ser Arg Asn Val Leu Val Ala Pro Thr Ser Met Leu Asp Gln Ser Leu Ser Ser Leu>
        ___c___c___c___c___c_____RECOMBINANT LEUKOTOXIN PEPTIDE_c___c___c___c___c___c___>

2770        2780        2790
           *     *     *     *     *     *
        CAA TTT GCT AGG GGA TCC TAG CTAGCTAGCCATGG
        GTT AAA CGA TCC CCT AGG ATC GATCGATCGGTACC
        Gln Phe Ala Arg Gly Ser End>
        ___RECOMBINANT LEUKOTOX____>
                       _b____VECTOR SEQUENCE_____>
```

FIG.5F

LEUKOTOXIN VACCINE COMPOSITIONS AND USES THEREOF

CROSS REFERENCE TO RELATED APPLICATION

This application is a continuation of application Ser. No. 08/015,537 filed on 9 February 1993, now U.S. Pat. No. 5,476,657, which is a continuation of application Ser. No. 07/504,850 filed on 5 April 1990, abandoned, which is a continuation-in-part of application Ser. No. 07/335,018 filed on 7 April 1989, abandoned.

TECHNICAL FIELD

The present invention relates generally to subunit antigens, vaccine compositions, and methods of administering the same. More particularly, the present invention relates to *Pasteurella haemolytica* proteins for use in stimulating immunity against pneumonia.

BACKGROUND OF THE INVENTION

Respiratory disease affecting feedlot cattle causes tremendous losses yearly to the cattle industry. Calves are the most severely affected, and a large number of these calves die. This disease is associated with pathogenic microorganisms, particularly *Pasteurellae* species, and various stresses, such as transportation and overcrowding.

Shipping fever is the most economically important respiratory disease associated with *Pasteurella* species. The disease is characterized by sudden onset, usually within two weeks of stress. The symptoms include dyspnea, cough, ocular and nasal discharge, inappetance and rapid weight loss, fever, increased lung sounds, immunosuppression, general depression, viral and/or bacterial infection of the lungs. Various bacteria and viruses have been isolated from affected animals including *Pasteurella* spp., bovine herpes virus 1, parainfluenza-3 virus, bovine respiratory syncytial virus and *Mycoplasma* species. The disease typically affects 15–30% of exposed animals and the resulting deaths are typically 2–5% of the exposed population.

Exposure of the animal to stress, plus infection with a variety of viruses, as described above, appears to make the animal susceptible to fibrinous pneumonia caused by *P. haemolytica*, and to a lesser extent, *Pasteurella multocida*. For a general background on shipping fever see Yates, W. D. G. (1982) *Can. J. Comp. Med.* 46:225–263.

*P. haemolytica* also causes enzootic pneumonia and can infect a wide range of animals, in addition to cattle, including economically important species such as sheep, swine, horses and fowl. *P. haemolytica* is also frequently found in the upper respiratory tract of healthy animals. Pneumonia develops when the bacteria infects the lungs of these animals. Protection against *Pasteurella*-associated diseases is therefore economically important to the agricultural industry.

There are two known biotypes of *P. haemolytica* designated A and T. There are also 12 recognized serotypes which have been isolated from ruminants. Biotype A, serotype 1 (referred to hereinafter as "A1") predominates in bovine pneumonia in North America. Shewen, P. E. and Wilkie, B. N. (1983) *Am. J. Vet. Res.* 44:715–719. However, antigens isolated from different serotypes appear to be somewhat cross-reactive. See, e.g., Donanchie et al. (1984) *J. Gen. Micro.* 130:1209–1216.

Previous *Pasteurellosis* vaccines have utilized whole cell preparations of either live or heat killed bacteria of various serotypes as described in U.S. Pat. Nos. 4,328,210, 4,171,354, 3,328,252, 4,167,560 and 4,346,074. Traditional vaccine preparations, however, have not been effective in protecting against *Pasteurella* infections. Indeed, vaccinated animals are frequently more susceptible to the disease than their non-vaccinated counterparts. Martin et al. (1980) *Can. J. Comp. Med.* 44:1–10. The lack of protection offered by traditional vaccines is probably due to the absence of important antigens, virulence determinants, or the presence of immunosuppressive components in the preparations.

Other vaccine preparations have included crude supernatant extracts from *P. haemolytica*. See, e.g., Shewen, P. E. and Wilkie, B. N. (1988) in *Can. J. Vet. Res.* 52:30–36. These culture supernatants, however, contain various soluble surface antigens of the bacterium and produce variable results when administered to animals. Other preparations include capsular extracts obtained via sodium salicylate extraction (See, e.g., Donanchie et al. (1984) 130:1209–1216; U.S. Pat. No. 4,346,074), saline extracted antigens (See, e.g., Lessley et al. (1985) *Veterinary Immunology and Immunopathology* 10:279–296; Himmel et al. (1982) *Am. J. Vet. Res.* 43:764–767), and modified live *Pasteurella* mutants.

Still other attempts at immunization have included the use of a purified cytotoxin from *P. haemolytica*. See, e.g. Gentry et al. (1985) *Vet. Immunology and Immunopathology* 9:239–250. This cytotoxin, which is a leukotoxin, is secreted by actively growing bacteria. Shewen, P. E., and Wilkie, B. N. (1987) *Infect. Immun.* 55:3233–3236. The gene encoding this leukotoxin has been cloned and expressed in bacterial cells. Lo et al. (1985) *Infect. Immun.* 50:667–671. Calves which survive *P. haemolytica* infections possess toxin-neutralizing anti-body. Cho, H. J. and Jericho, K. W. F. (1986) *Can. J. Vet. Res.* 50:27–31; Cho et al. (1984) *Can. J. Comp. Med.* 48:151–155.

Electron microscopy of intact *P. haemolytica* A-1 cells has demonstrated the presence of two types of fimbriae. Morck et al. (1987) *Can. J. Vet. Res.* 51:83–88. One type is rigid and easily sheared from the cell while the other is thin and flexible. The purpose of these fimbriae has not yet been determined. For some bacteria, however, fimbriae play a role in infection. See e.g. Normark et al. (1986) in *Protein-carbohydrate Interactions in Biological Systems* (D. Lark ed., 1986) pp. 3–12; Mooi, F. and deGraaf, F. K. (1985) Curr. Top. Microbiol. Immunol. 118:119–136.

Group A streptococci have recently been shown to possess a surface receptor that binds to host cell plasmin but not its precursor, plasminogen. Lottenberg et al. (1987) *Infect. Immun.* 55:1914–1928; Broeseker et al. (1988) *Microbial Pathogenesis* 5:19–27. Plasmin is a protease capable of hydrolyzing fibrin, extracellular matrix proteins and several plasma proteins. Therefore, it may be an important bacterial virulence mechanism and a potential immunogen.

DISCLOSURE OF THE INVENTION

It has been discovered that subunit vaccines based on selected cell surface antigens isolated from *P. haemolytica* protect cattle from respiratory diseases such as pneumonia, including shipping fever pneumonia, caused by this bacterium. These subunit vaccines appear to be substantially more protective than prior art vaccines. Furthermore, these subunit vaccines can be produced using recombinant DNA technology or by chemical extraction. Based on these discoveries, the present invention can take several embodiments.

In one embodiment, the present invention is directed to a vaccine composition including a pharmaceutically acceptable vehicle and a subunit antigen composition comprising at least one immunogenic polypeptide comprising an immunogenic amino acid sequence of a *P. haemolytica* protein, or an amino acid sequence substantially homologous and functionally equivalent thereto, selected from the group consisting of *P. haemolytica* fimbrial protein, *P. haemolytica* plasmin receptor protein, *P. haemolytica* 50K outer membrane protein, and *P. haemolytica* leukotoxin. Thus, any of these proteins may be used alone or in combination with one or more of the other disclosed proteins in a vaccine composition according to the present invention.

In another embodiment of the present invention, the vaccine composition includes a pharmaceutically acceptable vehicle, an adjuvant and a subunit antigen composition comprising an immunogenic polypeptide comprising an immunogenic amino acid sequence of *P. haemolytica* leukotoxin, or an amino acid sequence substantially homologous and functionally equivalent thereto, and a saline extract of *P. haemolytica*.

Other embodiments of the present invention include isolated *P. haemolytica* fimbrial protein, plasmin receptor protein and 50K outer membrane protein.

Still other embodiments of the instant invention include DNA constructs comprising an expression cassette including (a) a DNA coding sequence for a polypeptide containing at least one epitope of a *P. haemolytica* protein selected from the group consisting of *P. haemolytica* fimbrial protein, *P. haemolytica* plasmin receptor protein, and *P. haemolytica* 50K outer membrane protein; and (b) control sequences that are operably linked to the coding sequence whereby the coding sequence can be transcribed and translated in a host cell.

Another embodiment of the invention is directed to the plasmid pAA352 (ATCC No. 68283).

The present invention is also directed to host cells transformed with these constructs, as well as methods of making recombinant polypeptides useful in a *P. haemolytica* subunit vaccine.

In still other embodiments of the present invention, vaccination methods are provided for preventing or ameliorating respiratory disease in a ruminant.

These and other embodiments of the present invention will readily occur to those of ordinary skill in the art in view of the disclosure herein.

BRIEF DESCRIPTION OF THE FIGURES

FIG. 1 depicts the structure of the leukotoxin gene of *P. haemolytica* cloned in *E. coli* (Plasmid pAA114).

FIG. 2 depicts the structure of Plasmid pAA101.

FIG. 3 depicts the predicted amino acid sequence of the 1ktA::lacZ fusion protein from Plasmid pAA101. The portion representing the leukotoxin 1ktA protein is boxed.

FIGS. 5A–5F show the nucleotide sequence and predicted amino acid sequence of leukotoxin 352 (LKT 352) from plasmid pAA352. Both the structural gene for LKT 352 and the sequences of the flanking vector regions are shown.

DETAILED DESCRIPTION

Figure 4:
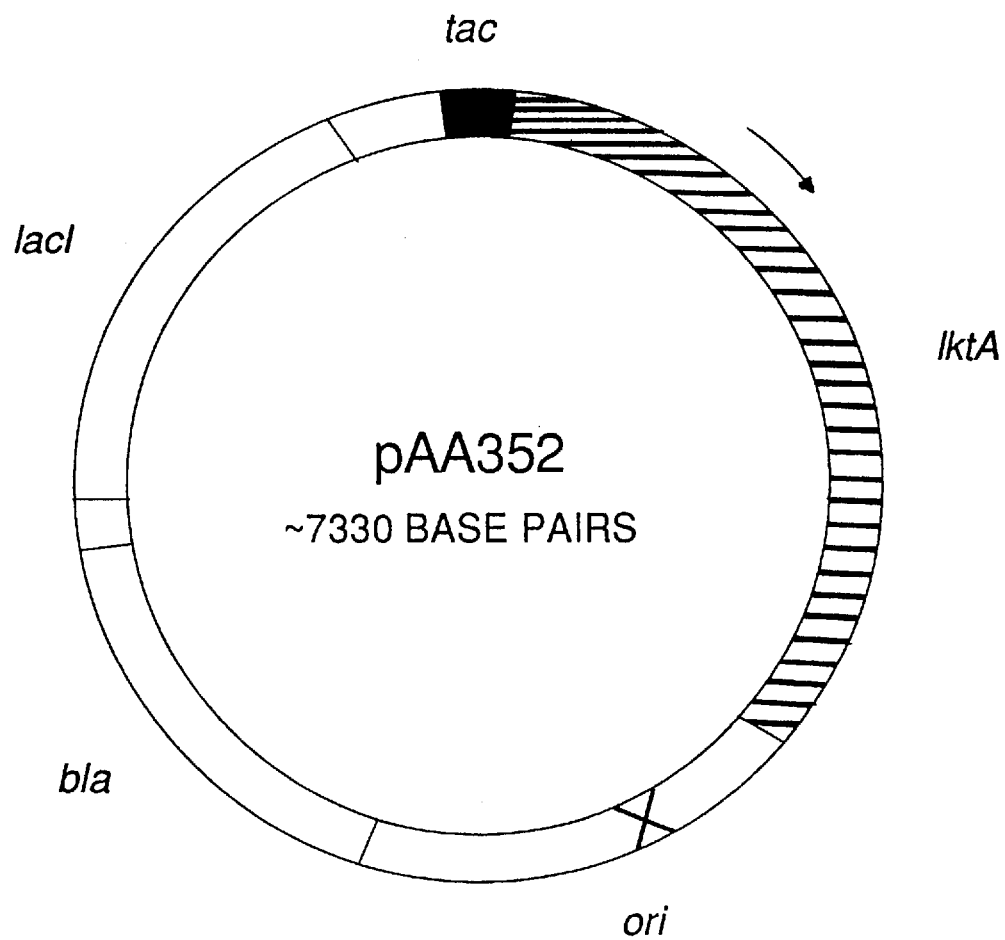
FIG. 4 depicts the structure of Plasmid pAA352 wherein tac is the hybrid trp::lac promoter from *E. coli*; bla represents the beta lactamase gene (ampicillin resistance); ori is the ColEl-based plasmid origin of replication; 1ktA is the *Pasteurella haemolytica* leukotoxin structural gene; and lacI is the *E. coli* lac operon repressor. The direction of transcription/translation of the leukotoxin gene is indicated by the arrow. The size of each component is not drawn to scale.

The practice of the present invention will employ, unless otherwise indicated, conventional techniques of molecular biology, microbiology, virology, recombinant DNA technology, and immunology, which are within the skill of the art. Such techniques are explained fully in the literature. See, e.g., Maniatis, Fritsch & Sambrook, *Molecular Cloning: A Laboratory Manual* (1982); *DNA Cloning*, Vols. I and II (D. N. Glover ed. 1985); *Oligonucleotide Synthesis* (M. J. Gait ed. 1984); *Nucleic Acid Hybridization* (B. D. Hames & S. J. Higgins eds. 1984); *Animal Cell Culture* (R. K. Freshney ed. 1986); *Immobilized Cells and Enzymes* (IRL press, 1986); B. Perbal, *A Practical Guide to Molecular Cloninq* (1984); the series, *Methods In Enzymology* (S. Colowick and N. Kaplan eds., Academic Press, Inc.); and *Handbook of Experimental Immunology*, Vols. I-IV (D. M. Weir and C. C. Blackwell eds., 1986, Blackwell Scientific Publications).

A. Definitions

In describing the present invention, the following terms will be employed, and are intended to be defined as indicated below.

An "antigen" refers to a molecule containing one or more epitopes that will stimulate a host's immune system to make a humoral and/or cellular antigen-specific response. The term is also used interchangeably with "immunogen."

A "hapten" is a molecule containing one or more epitopes that does not stimulate a host's immune system to make a humoral or cellular response unless linked to a carrier.

The term "antigenic determinant" refers to the site on an antigen or hapten to which a specific antibody molecule binds. The term is also used interchangeably with "epitope" or "antigenic determinant site."

An "immunological response" to a composition or vaccine is the development in the host of a cellular and/or antibody-mediated immune response to the composition or vaccine of interest. Usually, such a response consists of the subject producing antibodies, B cells, helper T cells, suppressor T cells, and/or cytotoxic T cells directed specifically to an antigen or antigens included in the composition or vaccine of interest.

An "immunogenic polypeptide" or "immunogenic amino acid sequence" is a polypeptide or amino acid sequence, respectively, which elicits an immunological response in a subject to which it is administered.

By "subunit antigen composition" is meant a composition containing at least one immunogenic polypeptide, but not all antigens, derived from or homologous to an antigen from a pathogen of interest. Such a composition is substantially free of intact pathogen cells or particles, or the lysate of such cells or particles. Rather, a "subunit antigen composition" is prepared from at least partially purified (preferably substantially purified) immunogenic polypeptides from the pathogen, or recombinant analogs thereof. Thus, a subunit antigen composition can comprise the subunit antigen or antigens of interest substantially free of other antigens or polypeptides from the pathogen.

A "substantially enriched" vaccine composition is one where an antigen is derived from a cellular source having an increased concentration of the desired antigen or antigens with respect to the concentration of antigen or antigens found under normal growth conditions. A composition can be "substantially enriched" by adding additional amounts of one or more of the antigens to the composition, by altering growth conditions to increase production of the desired antigen or antigens, or by selectively fractionating a cell lysate to enhance the amount of the desired antigen or antigens.

The term "protein" is used herein to designate a naturally occurring polypeptide. The term "polypeptide" is used in its broadest sense, i.e., any polymer of amino acids (dipeptide or greater) linked through peptide bonds. Thus, the term "polypeptide" includes proteins, oligopeptides, protein fragments, analogs, muteins, fusion proteins and the like.

"Native" proteins or polypeptides refer to proteins or polypeptides recovered from a source occurring in nature. Thus, the term "native *P. haemolytica* poly-peptide" would include naturally occurring *P. haemolytica* proteins and fragments thereof. "Recombinant" polypeptides refer to polypeptides produced by recombinant DNA techniques; i.e., produced from cells transformed by an exogenous DNA construct encoding the desired polypeptide. "Synthetic" polypeptides are those prepared by chemical synthesis.

A "replicon" is any genetic element (e.g., plasmid, chromosome, virus) that functions as an autonomous unit of DNA replication in vivo; i.e., capable of replication under its own control.

A "vector" is a replicon, such as a plasmid, phage, or cosmid, to which another DNA segment may be attached so as to bring about the replication of the attached segment.

A "double-stranded DNA molecule" refers to the polymeric form of deoxyribonucleotides (bases adenine, guanine, thymine, or cytosine) in a double-stranded helix, both relaxed and supercoiled. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having the sequence homologous to the mRNA).

A DNA "coding sequence" is a DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, procaryotic sequences, cDNA from eucaryotic mRNA, genomic DNA sequences from eucaryotic (e.g., mammalian) DNA, and even synthetic DNA sequences. A transcription termination sequence will usually be located 3' to the coding sequence.

A "promoter sequence" is a DNA regulatory region capable of binding RNA polymerase in a cell and initiating transcription of a downstream (3' direction) coding sequence. For purposes of defining the present invention, the promoter sequence is bound at the 3' terminus by the translation start codon (ATG) of a coding sequence and extends upstream (5' direction) to include the minimum number of bases or elements necessary to initiate transcription at levels detectable above background. Within the promoter sequence will be found a transcription initiation site (conveniently defined by mapping with nuclease Sl), as well as protein binding domains (consensus sequences) responsible for the binding of RNA polymerase. Eucaryotic promoters will often, but not always, contain "TATA" boxes and "CAT" boxes. Procaryotic promoters contain Shine-Dalgarno sequences in addition to the −10 and −35 consensus sequences.

DNA "control sequences" refers collectively to promoter sequences, ribosome binding sites, polyadenylation signals, transcription termination sequences, upstream regulatory domains, enhancers, and the like, which collectively provide for the transcription and translation of a coding sequence in a host cell.

A coding sequence is "operably linked to" or "under the control of" control sequences in a cell when RNA polymerase will bind the promoter sequence and transcribe the coding sequence into mRNA, which is then translated into the polypeptide encoded by the coding sequence.

A "host cell" is a cell which has been transformed, or is capable of transformation, by an exogenous DNA sequence.

A cell has been "transformed" by exogenous DNA when such exogenous DNA has been introduced inside the cell membrane. Exogenous DNA may or may not be integrated (covalently linked) to chromosomal DNA making up the genome of the cell. In procaryotes and yeasts, for example, the exogenous DNA may be maintained on an episomal element, such as a plasmid. With respect to eucaryotic cells, a stably transformed cell is one in which the exogenous DNA has become integrated into the chromosome so that it is inherited by daughter cells through chromosome replication. This stability is demonstrated by the ability of the eucaryotic cell to establish cell lines or clones comprised of a population of daughter cell containing the exogenous DNA.

A "clone" is a population of cells derived from a single cell or common ancestor by mitosis. A "cell line" is a clone of a primary cell that is capable of stable growth in vitro for many generations.

Two DNA or polypeptide sequences are "substantially homologous" when at least about 80% (preferably at least about 90%, and most preferably at least about 95%) of the nucleotides or amino acids match over a defined length of the molecule. DNA sequences that are substantially homologous can be identified in a Southern hybridization experiment under, for example, stringent conditions, as defined for that particular system. Defining appropriate hybridization conditions is within the skill of the art. See, e.g., Maniatis et al., supra; *DNA Cloning*, vols I & II, supra; *Nucleic Acid Hybridization*, supra.

The term "functionally equivalent" intends that the amino acid sequence of the subject polypeptide is one that will elicit an immunological response, as defined above, equivalent to a *P. haemolytica* immunogenic polypeptide.

A "heterologous" region of a DNA construct is an identifiable segment of DNA within or attached to another DNA molecule that is not found in association with the other molecule in nature. Thus, when the heterologous region encodes a bacterial gene, the gene will usually be flanked by DNA that does not flank the bacterial gene in the genome of the source bacteria. Another example of the heterologous coding sequence is a construct where the coding sequence itself is not found in nature (e.g., synthetic sequences having codons different from the native gene). Allelic variation or naturally occurring mutational events do not give rise to a heterologous region of DNA, as used herein.

A composition containing A is "substantially free of" B when at least about 85% by weight of the total of A+B in the composition is A. Preferably, A comprises at least about 90% by weight of the total of A+B in the composition, more preferably at least about 95%, or even 99% by weight.

The term "treatment" as used herein refers to either (i) the prevention of infection or reinfection (prophylaxis), or (ii) the reduction or elimination of symptoms or the disease of interest (therapy).

B. General Methods

Central to the instant invention is the discovery of several cell surface antigens of *P. haemolytica* including *P. haemolytica* fimbrial protein, *P. haemolytica* plasmin receptor protein, *P. haemolytica* 50K outer membrane protein and *P. haemolytica* leukotoxin. These proteins can be used, either alone or in combination, in a vaccine composition to protect animals against respiratory diseases such as pneumonia, including shipping fever pneumonia. Each of these proteins, or a mixture of two or more of the proteins, can be further combined with saline extracted antigens, sodium salicylate capsular extracts, or antigens extracted by other methods known in the art, to produce a vaccine useful in protecting an animal against shipping fever or other respiratory disease.

*P. haemolytica* bears at least two types of fimbriae or pili, one thick and rigid and the other thin and flexible. Such fimbriae can be isolated from bacteria grown under routine conditions. For example, fimbriae can be isolated from *P. haemolytica* cultures grown on brain heart infusion agar at 37° C. Additionally, it may be possible to enhance fimbrial growth by subjecting various bacteria to elevated temperatures or increased iron levels. Doorn et al. (1987) *Microbial Pathogenesis* 3:87–95.

Figure 6A:
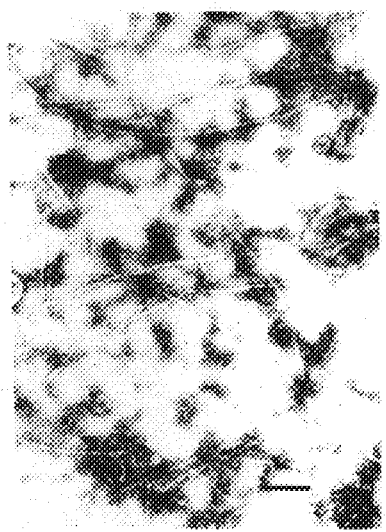
FIGS. 6A–6C represent electron micrographs of *P. haemolytica* strain B122 fimbrial fractions. The bar equals 100 nm. 6A shows PH-K fimbriae present in a crude shear fraction. 6B shows PH-K fimbriae following CsCl ultracentrifugation (density=1.32 g/ml). 6C shows PH-K fimbriae following CsCl ultracentrifugation and incubation with 5M urea.
Figure 6B:
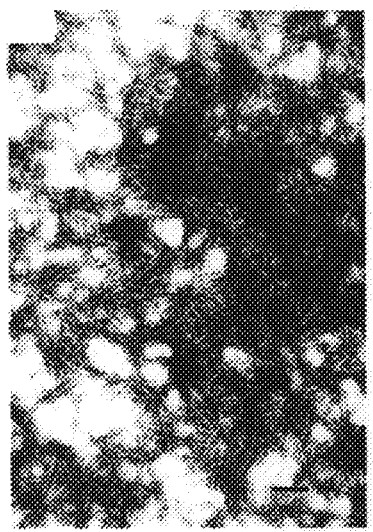

The thick and rigid fimbriae from *P. haemolytica* A1, referred to as "PH-K fimbriae," can be seen in a crude shear fraction as illustrated in FIG. 6A. The fraction can be further purified by centrifugation through a CsCl step gradient, rendering fimbrial structures as seen in FIG. 6B. The fimbriae thus isolated have a density of 1.32 and a molecular weight of approximately 35,000, as determined by SDS-polyacrylamide gel electrophoresis and immunoblotting with monoclonal antibodies raised against native fimbriae. The fimbriae are approximately 12 nm in diameter and vary in length from <100 nm to more than 500 nm. The isoelectric point of the purified fimbriae is 4.8.

The purified fimbrial protein includes the following amino acid sequence:

xxxxxxIle-Ala-Ala-Leu-Asn-Thr-Leu-Asn-Arg-Leu-Ser-Ala-Asn-Asn-Gly-Ala-Ser-Gln-Lys-Asn-(Met-Phe).

where x is unknown.

The fimbrial protein can also be purified using standard immunoadsorption techniques well known in the art. Additionally, the fimbrial protein can be produced via recombinant methods as described more fully below.

The protein has been used in vaccine trials as discussed in the experimental section and protects subjects from subsequent challenge with *P. haemolytica*.

Also of importance to the instant invention is the identification of a receptor protein on the surface of *P. haemolytica* able to bind both plasmin and plasminogen. Plasmin receptors have only recently been found in association with one other bacterium—group A streptococcus. See Lottenberg et al., supra; Broseker et al., supra. Furthermore, unlike *Pasteurella* receptors, plasmin receptors of group A streptococcus are unable to bind the inactive zymogen, plasminogen.

These plasmin receptors can be detected by adding *P. haemolytica* to a substrate known to be degraded by plasmin. For example, fibrin plate assays, casein degradation assays using skim milk-agarose plates, as well as other assays, well known in the art, can be used for this purpose. The identity of the receptor protein can further be established by using standard techniques including separation using electrophoretic techniques, electroblotting the components to a nitrocellulose membrane and reacting the products with biotinylated plasmin or plasminogen. Identification procedures are described more fully in the experimental section. The receptor has a molecular weight of approximately 41,000 as determined by SDS-PAGE. The receptor protein can also be purified via immunoadsorption or produced by recombinant means as discussed below.

Also of importance is the discovery of a new outer membrane protein of *P. haemolytica*. This protein has a molecular weight of 50,000 as determined by SDS-PAGE. Immunologically-related proteins of the same molecular weight are produced by *P. haemolytica* serotypes 1, 2, 5, 6, 7, 8, 9 and 12. The protein can be purified by elution from polyacrylamide gels of separated outer membrane components. This protein, alone or in combination with the proteins described above, is useful in protecting subjects from subsequent challenge with bovine herpes virus-1 followed by exposure to *P. haemolytica*.

Also useful in the vaccines of the present invention is *P. haemolytica* leukotoxin. Actively growing cells of *P. haemolytica* have been shown to secrete leukotoxin which can also be cloned, expressed and used either alone or in combination with one or more of the above antigens to immunize subjects against shipping fever. The nucleotide sequence coding for *P. haemolytica* A1 leukotoxin has been determined. See, e.q., Lo, R. Y. C. (1987) *Infect. Immun.* 55:1987–1996. Of interest is the fact that the *P. haemolytica* leukotoxin gene and the corresponding protein share extensive homology with *Escherichia coli* alpha hemolysin (50.3% of the amino acid residues are identical). Strathdee, C. A., and Lo, R. Y. C. (1987) *Infect. Immun.* 55:3233–3236. *P. haemolytica* leukotoxin can be produced using recombinant techniques and purified from, for example, bacterial cells. The leukotoxin can also be purified from native bacteria using immunoadsorbent chromatography. The molecular weight of the purified leukotoxin is approximately 95,000 and the isoelectric point is 6.3.

Saline extracts of *P. haemolytica* can also be combined with any of the above subunit antigens. These extracts are produced by extracting proteins in an 0.85% (w/v) sodium chloride solution. The extract can be further treated, i.e. with glass beads and agitation, or other methods known in the art, to remove cell surface proteins. The combination of such saline extracts with isolated or recombinantly produced leukotoxin affords potent protection against shipping fever.

Purification of the above antigens as described herein permits the sequencing of the same by any of the various methods known to those skilled in the art. For example, the amino acid sequences of the subject proteins can be determined from the purified proteins by repetitive cycles of Edman degradation, followed by amino acid analysis by HPLC. Other methods of amino acid sequencing are also known in the art.

Once the amino acid sequences are determined, oligonucleotide probes which contain the codons for a portion of the determined amino acid sequences can be prepared and used to screen DNA libraries for genes encoding the subject proteins. The basic strategies for preparing oligonucleotide probes and DNA libraries, as well as their screening by nucleic acid hybridization, are well known to those of ordinary skill in the art. See, e.g., *DNA Cloning*: Vol. I, supra; *Nucleic Acid Hybridization*, supra; *Oligonucleotide Synthesis*, supra; T. Maniatis et al., supra.

First, a DNA library is prepared. The library can consist of a genomic DNA library from *P. haemolytica*. Once the library is constructed, oligonucleotides to probe the library are prepared and used to isolate the gene encoding the desired protein. The oligonucleotides are synthesized by any appropriate method. The particular nucleotide sequences selected are chosen so as to correspond to the codons encoding a known amino acid sequence from the desired *P. haemolytica* protein. Since the genetic code is degenerate, it will often be necessary to synthesize several oligonucleotides to cover all, or a reasonable number, of the possible nucleotide sequences which encode a particular region of the protein. Thus, it is generally preferred in selecting a region upon which to base the probes, that the region not contain amino acids whose codons are highly degenerate. In certain circumstances, one of skill in the art may find it desirable to prepare probes that are fairly long, and/or encompass regions of the amino acid sequence which would have a high degree of redundancy in corresponding nucleic acid sequences, particularly if this lengthy and/or redundant region is highly characteristic of the protein of interest. It may also be desirable to use two probes (or sets of probes), each to different regions of the gene, in a single hybridization experiment. Automated oligonucleotide synthesis has made the preparation of large families of probes relatively straightforward. While the exact length of the probe employed is not critical, generally it is recognized in the art that probes from about 14 to about 20 base pairs are usually effective. Longer probes of about 25 to about 60 base pairs are also used.

The selected oligonucleotide probes are labeled with a marker, such as a radionucleotide or biotin using standard procedures. The labeled set of probes is then used in the screening step, which consists of allowing the single-stranded probe to hybridize to isolated ssDNA from the library, according to standard techniques. Either stringent or permissive hybridization conditions could be appropriate, depending upon several factors, such as the length of the probe and whether the probe is derived from the same species as the library, or an evolutionarily close or distant species. The selection of the appropriate conditions is within the skill of the art. See generally, *Nucleic Acid hybridization*, supra. The basic requirement is that hybridization conditions be of sufficient stringency so that selective hybridization occurs; i.e., hybridization is due to a sufficient degree of nucleic acid homology (e.g., at least about 75%), as opposed to nonspecific binding. Once a clone from the screened library has been identified by positive hybridization, it can be confirmed by restriction enzyme analysis and DNA sequencing that the particular library insert contains a gene for the desired protein.

Alternatively, DNA sequences encoding the proteins of interest can be prepared synthetically rather than cloned. The DNA sequence can be designed with the appropriate codons for the particular *Pasteurella* amino acid sequence. In general, one will select preferred codons for the intended host if the sequence will be used for expression. The complete sequence is assembled from overlapping oligonucleotides prepared by standard methods and assembled into a complete coding sequence. See, e.g., *Edge* (1981), *Nature* 292:756; Nambair et al. (1984) *Science* 223:1299; Jay et al. (1984) *J. Biol. Chem.* 259:6311.

Once a coding sequence for the desired protein has been prepared or isolated, it can be cloned into any suitable vector or replicon. Numerous cloning vectors are known to those of skill in the art, and the selection of an appropriate cloning vector is a matter of choice. Examples of recombinant DNA vectors for cloning and host cells which they can transform include the bacteriophage lambda (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillus subtilis*), pBD9 (*Bacillus*), pIJ61 (*Streptomyces*), pUC6 (*Streptomyces*), YIp5 (*Saccharomyces*), YCp19 (*Saccharomyces*) and bovine papilloma virus (mammalian cells). See, generally, *DNA Cloning*: Vols. I & II, supra; T. Maniatis et al., supra; B. Perbal, supra.

The coding sequence for the *Pasteurella* protein of interest can be placed under the control of a promoter, ribosome binding site (for bacterial expression) and, optionally, an operator (collectively referred to herein as "control" elements), so that the DNA sequence encoding the protein is transcribed into RNA in the host cell transformed by a vector containing this expression construction. The coding sequence may or may not contain a signal peptide or leader sequence. The full length *P. haemolytica* proteins of the present invention can be expressed using, for example, native *P. haemolytica* promoter or the protein A gene (spa) promoter and signal sequence. Truncated versions of the genes of interest can be fusions with the B-galactosidase gene (lacz) as well as genes coding for galactokinase (galK) and interleukin-2 (bovine). Leader sequences can be removed by the bacterial host in post-translational processing. See, e.g., U.S. Pat. Nos. 4,431,739; 4,425,437; 4,338,397.

In addition to control sequences, it may be desirable to add regulatory sequences which allow for regulation of the expression of the bacterial antigen sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences. The subject proteins can also be expressed in the form of a fusion protein, wherein a heterologous amino acid sequence is expressed at the N-terminal. See, e.g., U.S. Pat. Nos. 4,431,739; 4,425,437.

An expression vector is constructed so that the particular coding sequence is located in the vector with the appropriate regulatory sequences, the positioning and orientation of the coding sequence with respect to the control sequences being such that the coding sequence is transcribed under the "control" of the control sequences (i.e., RNA polymerase which binds to the DNA molecule at the control sequences transcribes the coding sequence). Modification of the sequences encoding the particular antigen of interest may be desirable to achieve this end. For example, in some cases it may be necessary to modify the sequence so that it may be attached to the control sequences with the appropriate orientation; i.e., to maintain the reading frame. The control sequences and other regulatory sequences may be ligated to the coding sequence prior to insertion into a vector, such as the cloning vectors described above. Alternatively, the coding sequence can be cloned directly into an expression vector which already contains the control sequences and an appropriate restriction site.

In some cases, it may be desirable to add sequences which cause the secretion of the polypeptide from the host organism, with subsequent cleavage of the secretory signal. It may also be desirable to produce mutants or analogs of the antigen of interest. Mutants or analogs may be prepared by the deletion of a portion of the sequence encoding the antigen, by insertion of a sequence, and/or by substitution of one or more nucleotides within the sequence. Techniques for modifying nucleotide sequences, such as site-directed mutagenesis, are well known to those skilled in the art. See, e.g., T. Maniatis et al., supra; *DNA Cloning*, Vols. I and II, supra; *Nucleic Acid Hybridization*, supra.

A number of procaryotic expression vectors are known in the art. See, e.g., U.S. Pat. Nos. 4,440,859; 4,436,815; 4,431,740; 4,431,739; 4,428,941; 4,425,437; 4,418,149; 4,411,994; 4,366,246; 4,342,832; see also U.K. Patent Applications GB 2,121,054; GB 2,008,123; GB 2,007,675; and European Patent Application 103,395. Yeast expression vectors are also known in the art. See, e.g., U.S. Pat. Nos. 4,446,235; 4,443,539; 4,430,428; see also European Patent Applications 103,409; 100,561; 96,491.

Depending on the expression system and host selected, the proteins of the present invention are produced by growing host cells transformed by an expression vector described above under conditions whereby the protein of interest is expressed. The particular *Pasteurella* protein is then isolated from the host cells and purified. If the expression system secretes the protein into growth media, the protein can be purified directly from the media. If the protein is not secreted, it is isolated from cell lysates. The selection of the appropriate growth conditions and recovery methods are within the skill of the art.

An alternative method to identify antigens of the present invention is by constructing gene libraries, using the resulting clones to transform *E. coli* and pooling and screening individual colonies using polyclonal serum or monoclonal antibodies to the desired antigen.

The antigens of the present invention can also be isolated from *P. haemolytica* cultures using standard protein purification procedures well known in the art. See, e.g., *Protein Purification Principles and Practice* 2d edition (Robert K. Scopes ed. 1987). Such techniques include gel filtration chromatography, ion exchange chromatography, affinity chromatography, immunoadsorbent chromatography, polyacrylamide gel electrophoresis and other electrophoretic techniques, centrifugation, dialysis, and precipitation.

The antigens of the present invention may also be produced by chemical synthesis such as solid phase peptide synthesis, using known amino acid sequences or amino acid sequences derived from the DNA sequence of the gene of interest. Such methods are known to those skilled in the art. Chemical synthesis of peptides may be preferable if a small fragment of the antigen in question is capable of raising an immunological response in the subject of interest.

The proteins of the present invention or their fragments can be used to produce antibodies, both polyclonal and monoclonal. If polyclonal antibodies are desired, a selected mammal, (e.g., mouse, rabbit, goat, horse, etc.) is immunized with an antigen of the present invention, or its fragment, or a mutated antigen. Serum from the immunized animal is collected and treated according to known procedures. If serum containing polyclonal antibodies is used, the polyclonal antibodies can be purified by immunoaffinity chromatography, using known procedures.

Monoclonal antibodies to the proteins of the present invention, and to the fragments thereof, can also be readily produced by one skilled in the art. The general methodology for making monoclonal antibodies by hybridomas is well known. Immortal antibody-producing cell lines can be created by cell fusion, and also by other techniques such as direct transformation of B lymphocytes with oncogenic DNA, or transfection with Epstein-Barr virus. See, e.g., M. Schreier et al., *Hybridoma Techniques* (1980); Hammerling et al., *Monoclonal Antibodies and T-cell Hybridomas* (1981); Kennett et al., *Monoclonal Antibodies* (1980); see also U.S. Pat. Nos. 4,341,761; 4,399,121; 4,427,783; 4,444,887; 4,452,570; 4,466,917; 4,472,500, 4,491,632; and 4,493,890. Panels of monoclonal antibodies produced against the antigen of interest, or fragment thereof, can be screened for various properties; i.e., for isotype, epitope, affinity, etc. Monoclonal antibodies are useful in purification, using immunoaffinity techniques, of the antigens which they are directed against.

Animals can be immunized with the compositions of the present invention by administration of the protein of interest, or a fragment thereof, or an analog thereof. If the fragment or analog is used, it will include the amino acid sequence of the epitope which interacts with the immune system to immunize the animal to that and structurally similar epitopes.

Fragments used to immunize a subject contain at least 6–30 amino acids which form the sequence of the desired protein, and include the particular epitope. Smaller fragments encompassing the epitope may be inserted into larger peptides or polypeptides, such that the regions flanking the epitope are not those that are encoded within the naturally occurring genes. The techniques for the synthesis of these peptides or polypeptides are apparent to one of average skill in the art. For example, the genetic sequence encoding a particular antigen may be isolated via cloning, and that sequence altered at sites other than that encoding the particular epitope. This alteration may be accomplished by site specific mutation, or by deletions, or by insertions. Alternatively, an oligonucleotide sequence encoding the epitope may be inserted into or attached to another sequence which encodes a different peptide or polypeptide. A recombinant sequence is then inserted into an expression vector which is compatible with the host to be transformed, and the expression system used to synthesize the desired peptide which includes the particular epitope. The techniques by which this may be accomplished are known to those of skill in the art. See, e.g., T. Maniatis et al., supra; *DNA Cloning*, Vols. I and II, supra; and *Nucleic Acid Hybridization*, supra. Alternatively, an oligopeptide may be synthesized by solid phase synthesis which includes the particular epitope, but which adds flanking amino acids to it which are not in the sequence of the naturally occurring antigen.

Prior to immunization, it may be desirable to increase the immunogenicity of the particular *Pasteurella* protein, or an analog of the protein, or particularly fragments of the protein. This can be accomplished in any one of several ways known to those of skill in the art. For example, the antigenic peptide may be administered linked to a carrier. For example, a fragment may be conjugated with a macromolecular carrier. Suitable carriers are typically large, slowly metabolized macromolecules such as: proteins; polysaccharides, such as sepharose, agarose, cellulose, cellulose beads and the like; polymeric amino acids such as polyglutamic acid, polylysine, and the like; amino acid copolymers; and inactive virus particles. Especially useful protein substrates are serum albumins, keyhole limpet hemocyanin, immunoglobulin molecules, thyroglobulin, ovalbumin, and other proteins well known to those skilled in the art.

The protein substrates may be used in their native form or their functional group content may be modified by, for example, succinylation of lysine residues or reaction with Cys-thiolactone. A sulfhydryl group may also be incorporated into the carrier (or antigen) by, for example, reaction of amino functions with 2-iminothiolane or the N-hydroxysuccinimide ester of 3-(4-dithiopyridyl propionate. Suitable carriers may also be modified to incorporate spacer arms (such as hexamethylene diamine or other bifunctional molecules of similar size) for attachment of peptides.

Other suitable carriers for the proteins/fragments/analogs of the present invention include VP6 polypeptides of rotaviruses, or functional fragments thereof, as disclosed in U.S. Pat. No. 5,071,651, incorporated herein by reference. Also useful is a fusion product of a viral protein and the epitope of interest made by methods disclosed in U.S. Pat. No. 4,722,840. Still other suitable carriers include cells, such as lymphocytes, since presentation in this form mimics the natural mode of presentation in the subject, which gives rise to the immunized state. Alternatively, the antigens of the present invention, or an antigenic fragment thereof, or analog thereof, may be coupled to erythrocytes, preferably the subject's own erythrocytes. Methods of coupling peptides to proteins or cells are known to those of skill in the art.

It is also possible to immunize a subject with a protein of the present invention, or a protective fragment thereof, or an analog thereof, which is administered alone, or mixed with a pharmaceutically acceptable vehicle or excipient. Typically, vaccines are prepared as injectables, either as liquid solutions or suspensions; solid forms suitable for solution in, or suspension in, liquid vehicles prior to injection may also be prepared. The preparation may also be emulsified or the active ingredient encapsulated in liposome vehicles. The active immunogenic ingredient is often mixed with vehicles containing excipients which are pharmaceutically acceptable and compatible with the active ingredient. Suitable vehicles are, for example, water, saline, dextrose, glycerol, ethanol, or the like, and combinations thereof. In addition, if desired, the vehicle may contain minor amounts of auxiliary substances such as wetting or emulsifying agents, pH buffering agents, or adjuvants which enhance the effectiveness of the vaccine. Adjuvants may include for example, muramyl dipeptides, avridine, aluminum hydroxide, oils, saponins and other substances known in the art. Actual methods of preparing such dosage forms are known, or will be apparent, to those skilled in the art. See, e.q., Remington's Pharmaceutical Sciences, Mack Publishing Company, Easton, Pa., 15th edition, 1975. The composition or formulation to be administered will, in any event, contain a quantity of the protein adequate to achieve the desired immunized state in the individual being treated.

Additional vaccine formulations which are suitable for other modes of administration include suppositories and, in some cases, aerosol, intranasal and oral formulations. For suppositories, the vehicle composition will include traditional binders and carriers, such as, polyalkaline glycols, or triglycerides. Such suppositories may be formed from mixtures containing the active ingredient in the range of about 0.5% to about 10% (w/w), preferably about 1% to about 2%. Oral vehicles include such normally employed excipients as, for example, pharmaceutical grades of mannitol, lactose, starch, magnesium, stearate, sodium saccharin cellulose, magnesium carbonate, and the like. These oral vaccine compositions may be taken in the form of solutions, suspensions, tablets, pills, capsules, sustained release formulations, or powders, and contain from about 10% to about 95% of the active ingredient, preferably about 25% to about 70%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

Furthermore, the *P. haemolytica* antigens (or complexes thereof) may be formulated into vaccine compositions in either neutral or salt forms. Pharmaceutically acceptable salts include the acid addition salts (formed with the free amino groups of the active polypeptides) and which are formed with inorganic acids such as, for example, hydrochloric or phosphoric acids, or such organic acids as acetic, oxalic, tartaric, mandelic, and the like. Salts formed from free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

To immunize a subject, the polypeptide of interest, or an immunologically active fragment thereof, is administered parenterally, usually by intramuscular injection in an appropriate vehicle. Other modes of administration, however, such as subcutaneous, intravenous injection and intranasal delivery, are also acceptable. Injectable vaccine formulations will contain an effective amount of the active ingredient in a vehicle, the exact amount being readily determined by one skilled in the art. The active ingredient may typically range from about 1% to about 95% (w/w) of the composition, or even higher or lower if appropriate. The quantity to be administered depends on the animal to be treated, the capacity of the animal's immune system to synthesize antibodies, and the degree of protection desired. It has been found that in the present vaccine formulations, 50 ug of active ingredient per ml of injected solution is adequate to raise an immunological response when a dose of 1 to 5 ml per animal is administered. Other effective dosages can be readily established by one of ordinary skill in the art through routine trials establishing dose response curves. The subject is immunized by administration of the particular antigen or fragment thereof, or analog thereof, in at least one dose, and preferably two doses. Moreover, the animal may be administered as many doses as is required to maintain a state of immunity to pneumonia.

Below are examples of specific embodiments for carrying out the present invention. The examples are offered for illustrative purposes only, and are not intended to limit the scope of the present invention in any way.

Deposits of Strains Useful in Practicing the Invention

A deposit of biologically pure cultures of the following strains was made with the American Type Culture Collection, 12301 Parklawn Drive, Rockville, Md. The accession number indicated was assigned after successful viability testing, and the requisite fees were paid. Access to said cultures will be available during pendency of the patent application to one determined by the Commissioner to be entitled thereto under 37 CFR 1.14 and 35 USC 122. All restriction on availability of said cultures to the public will be irrevocably removed upon the granting of a patent based upon the application. Moreover, the designated deposits will be maintained for a period of thirty (30) years from the date of deposit, or for five (5) years after the last request for the deposit; or for the enforceable life of the U.S. patent, whichever is longer. Should a culture become nonviable or be inadvertently destroyed, or, in the case of plasmid-containing strains, lose its plasmid, it will be replaced with a viable culture(s) of the same taxonomic description.

| Strain | Deposit Date | ATCC No. |
| --- | --- | --- |
| P. haemolytica serotype 1 B122 | February 1, 1989 | 53863 |
| pAA213 in E. coli JM105 | February 1, 1989 | 67882 |
| pAA101 in E. coli JM105 | February 1, 1989 | 67883 |
| pAA352 in E. coli W1485 | March 30, 1990 | 68283 |

C. Experimental

Materials and Methods

Enzymes were purchased from commercial sources, and used according to the manufacturers' directions. Radionucleotides and nitrocellulose filters were also purchased from commercial sources.

In the cloning of DNA fragments, except where noted, all DNA manipulations were done according to standard procedures. See T. Maniatis et al., supra. Restriction enzymes, $T_4$ DNA ligase, E. coli, DNA polymerase I, Klenow fragment, and other biological reagents were purchased from commercial suppliers and used according to the manufacturers' directions. Double-stranded DNA fragments were separated on agarose gels.

cDNA and genomic libraries were prepared by standard techniques in pUC13 and the bacteriophage lambda gt11, respectively. See DNA CLONING: Vols I and II, supra.

P. haemolytica biotype A, serotype 1 ("A1") strain B122 was isolated from the lung of a calf which died of pneumonic pasteurellosis and was stored at −70° C. in defibrinated blood. Routine propagation was carried out on blood agar plates or in brain heart infusion broth (Difco Laboratories, Detroit, Mich.) supplemented with 5% (v/v) horse serum (Gibco Canada Ltd., Burlington, Canada). All cultures were incubated at 37° C.

EXAMPLE 1

The protective capacity of P. haemolytica leukotoxin and 50K outer membrane protein were tested by administering the recombinant and/or authentic products listed in Table 1 to calves.

Table 1

Proteins Administered To Calves In Example 1

(1) Recombinant 50K outer membrane protein.
(2) Control group—avridine (adjuvant) only.
(3) Authentic leukotoxin.
(4) Recombinant leukotoxin:B-galactosidase (from pAA101 described below).
(5) Recombinant leukotoxin (from pAA352 described below).
(6) Recombinant 50K outer membrane protein plus authentic leukotoxin.
(7) Recombinant outer membrane protein plus recombinant leukotoxin.
(8) Saline-extract of P. haemolytica.
(9) Saline-extract plus authentic leukotoxin.
(10) Saline-extract plus recombinant leukotoxin (from pAA352).

The products from Table 1 were made as follows.

Purification of P. haemolytica Authentic Leukotoxin

P. haemolytica A1 was grown to mid-log phase in Brain Heart Infusion broth (Difco) at 37° C. Cells were harvested by centrifuging at 9,000 rpm for 20 minutes using a Sorval GSA rotor. The supernatant was transferred to a fresh flask and ammonium sulfate added to 70% saturation. The mixture was stirred overnight in the cold. The precipitate was collected by centrifugation as above and the pellet was dissolved in 10 ml sterile water per liter of the original culture. The dissolved pellet was desalted by passage through Sephadex G-25. The collected sample was subjected to preparative isoelectric focusing using a rotofor apparatus (Biorad Labs) over a pH gradient of 5 to 7. Fractions over a range of pH 6–7 were pooled and NaCl added to 1.0M. The sample was passed through a Sephadex G-25 column. The purified leukotoxin was loaded on a 12.5% SDS-polyacrylamide gel and the sample contained one major protein band corresponding to a molecular weight of 95,000.

1. Production of P. haemolytica Recombinant Leukotoxin from pAA101

To produce recombinant leukotoxin, gene libraries of P. haemolytica A1 (strain B122) were constructed using standard techniques. See Lo et al., Infect. Immun., supra; DNA CLONING: Vols. I and II, supra; and T. MANIATIS et al., supra. A genomic library was constructed in the plasmid vector pUC13 and a DNA library constructed in the bacteriophage lambda gt11. The resulting clones were used to transform E. coli and individual colonies were pooled and screened for reaction with serum from a calf which had survived a P. haemolytica infection and that had been boosted with a concentrated culture supernatant of P. haemolytica to increase anti-leukotoxin anti-body levels. Positive colonies were screened for their ability to produce leukotoxin by incubating cell lysates with bovine neutrophils and subsequently measuring release of lactate dehydrogenase from the latter.

Several positive colonies were identified and these recombinants were analyzed by restriction endonuclease mapping. One clone appeared to be identical to a leukotoxin gene cloned previously. See Lo et al., Infect. Immun, supra. To confirm this, smaller fragments were recloned and the restriction maps compared. It was determined that approximately 4 kilobase pairs of DNA had been cloned. Progressively larger clones were isolated by carrying out a chromosome walk (5' to 3' direction) in order to isolate full length recombinants which were approximately 8 kb in length. The final construct was termed pAA114. This construct contained the entire leukotoxin gene sequence. The structure of this plasmid is shown in FIG. 1.

Both full length and truncated versions of the leukotoxin gene were expressed. The truncated forms were fusions with B-galactosidase (lacZ). The full length versions were expressed using the native P. haemolytica promoter or the protein A gene (spa) promoter and signal sequence. Clones were constructed as follows.

Plasmids pLTX1.1 and pLTX3.2 were isolated from *P. haemolytica* genomic DNA as purified restriction fragments (1.0 kb and 2.1 kb, respectively) from an EcoRV Pst1 double digest. These fragments were cloned into pTZ18R digested with HincII Pst1. The vector was used to transform *E. coli* strain JM105. Transformed cells were identified by plating on media containing ampicillin plus Xgal and IPTG. Blue colonies indicated the presence of a functional lacz gene. The DNA from these colonies was analyzed by restriction endonuclease digestion and found to contain the 5' end of the leukotoxin gene (lktC+lktA). This plasmid was termed pLTX3P.1.

Plasmid pLTX3P.1 was mutagenized in vitro with hydroxylamine, transformed into JM105 and plated on a growth medium containing ampicillin plus a reduced concentration of Xgal. In this way clones expressing increased quantities of the lktA:lacZ product would be dark blue whereas those containing an unmodified gene would be white or light blue. The clones from the dark blue colonies were termed pAA134.

A leukotoxin EcoRV/Pst1 5'-fragment (from pLTX3P.1) was subcloned into pBR325 digested with EcoR1/Pst1 containing the native leukotoxin promoter (from pLTX3P.1), plus a promoterless full length lacZ gene from plasmid pMC1871 (Pst1 fragment). The plasmid was used to transform *E. coli* JM105 and blue colonies were isolated from Xgal agar. This plasmid was termed pAA101 and is illustrated in FIG. 2. The predicted amino acid sequence of the fusion protein is shown in FIG. 3.

2. Production of *P. haemolytica* Recombinant Leukotoxin from pAA352

A second version of recombinant *P. haemolytica* leukotoxin was expressed. This leukotoxin was termed "leukotoxin 352" or "LKT 352". In order to produce this leukotoxin, the following gene construct was prepared from pAA114 described above.

lktA, a MaeI restriction endonuclease fragment which contained the entire gene was treated with the Klenow fragment of DNA polymerase I plus nucleotide triphosphates and ligated into the SmaI site of the cloning vector pUC13. This plasmid was named pAA179. From this, two expression constructs were made in the ptac-based vector pGH432: lacI digested with SmaI. One, pAA342, consisted of the 5'-AhaIII fragment of the lktA gene while the other, pAA345, contained the entire MaeI fragment described above. The clone pAA342 expressed a truncated leukotoxin peptide at high levels while pAA345 expressed full length leukotoxin at very low levels. Therefore, the 3' end of the lktA gene (StyI BamHI fragment from pAA345) was ligated to StyI BamHI-digested pAA342, yielding the plasmid pAA352. The structure of this plasmid is shown in FIG. 4.

The nucleotide sequence of the leukotoxin expressed by plasmid pAA352 (LKT 352 or new leukotoxin) is shown in FIGS. 5a–5F. The peptide encoded by this sequence is 931 amino acids in length and is 98% homologous to authentic leukotoxin. This recombinant leukotoxin migrates, on polyacrylamide gels, to a position identical to authentic leukotoxin.

3.a. Purification of Recombinant Leukotoxin from Example 1.1

Two liters of *E. coli* JM105/pAA101 were grown in broth to mid-exponential growth phase and the cells harvested by centrifugation. The pellet was resuspended in 50 ml of TEP buffer (100 mM Tris-HCl, pH 7.4, 10 mM EDTA, 1 mM phenyl methyl sulfonyl fluoride), immediately frozen at $-70°$ C. and held overnight. The cells were then thawed and sonicated for a total of 4 minutes (30 second bursts, 200 W) and the cell debris removed by centrifugation at 10,000 rpm in a Sorvall SS-34 rotor. The supernatant was mixed with three volumes of saturated ammonium sulfate and stirred at $4°$ C. for 60 minutes. This slurry was stored at $4°$ C. overnight then centrifuged as above. The pellet obtained from *E. coli* JM105/pAA101 cells was dissolved in 10 ml of TEP buffer and diluted to 20 ml with TBSN (10 mM Tris-HCl, pH 8, 500 mM NaCl, 0.2% NP-40). This solution was passed through an affinity column containing a monoclonal antibody to B-galactosidase ("Protosorb" from Promega Biotech). The column was washed once with 20 ml TBSN. The fusion protein was eluted with 5.0 ml of 0.1M $NaHCO_3/Na_2CO_3$, pH 10.8, and stored at $4°$ C.

3.b. Purification of Recombinant Leukotoxin (LKT 352) from Example 1.2

Recombinant LKT 352 was purified using the following procedure. Five to ten colonies of *E. coli* W1485/pAA352 (ATCC no. 68283) were inoculated into 10 ml of TB broth supplemented with 100 micrograms/ml of ampicillin and incubated at $37°$ C. for 6 hours on a G10 shaker, 220 rpm. Four ml of this culture was diluted into each of two baffled Fernbach flasks containing 400 ml of TB broth+ampicillin and incubated overnight as described above. Cells were harvested by centrifugation for 10 minutes at 4,000 rpm in polypropylene bottles, 500 ml volume, using a Sorvall GS3 rotor. The pellet was resuspended in an equal volume of TB broth containing ampicillin which had been prewarmed to $37°$ C. (i.e., 2×400 ml), and the cells were incubated for 2 hours as described above.

3.2 ml of isopropyl-B,D-thiogalactopyranoside (IPTG, Gibco/BRL), 500 mM in water (final concentration=4 mM), was added to each culture in order to induce synthesis of recombinant leukotoxin. Cultures were incubated for two hours. Cells were harvested by centrifugation as described above, resuspended in 30 ml of 50 mM Tris-hydrochloride, 25% (w/v) sucrose, pH 8.0, and frozen at $-70°$ C. The frozen cells were thawed at room temperature after 60 minutes at $-70°$ C., and 5 ml of lysozyme (Sigma, 20 mg/ml in 250 mM Tris-HCl, pH 8.0) was added. The mixture was vortexed at high speed for 10 seconds and then placed on ice for 15 minutes. The cells were then added to 500 ml of lysis buffer in a 1000 ml beaker and mixed by stirring with a 2 ml pipette. The beaker containing the lysed cell suspension was placed on ice and sonicated for a total of 2.5 minutes (5–30 second bursts with 1 minute cooling between each) with a Braun sonicator, large probe, set at 100 watts power. Equal volumes of the solution were placed in Teflon SS34 centrifuge tubes and centrifuged for 20 minutes at 10,000 rpm in a Sorvall SS34 rotor. The pellets were resuspended in a total of 100 ml of sterile double distilled water by vortexing at high speed, and the centrifugation step repeated. Supernatants were discarded and the pellets combined in 20 ml of 10 mM Tris-HCl, 150 mM NaCl, pH 8.0 (Tris-buffered saline) and the suspension frozen overnight at $-20°$ C.

The recombinant leukotoxin suspension was thawed at room temperature and added to 100 ml of 8M Guanidine HCl (Sigma) in Tris-buffered saline and mixed vigorously. A magnetic stir bar was placed in the bottle and the solubilized sample was mixed at room temperature for 30 minutes. The solution was transferred to a 2000 ml Ehrlenmyer flask and 1200 ml of Tris-buffered saline was quickly added. This mixture was stirred at room temperature for an additional 2 hours. 500 ml aliquots were placed in dialysis bags (Spectrum, 63.7 mm diameter, 6,000–8,000 MW cutoff, #132670, from Fisher scientific) and these were placed in 4,000 ml beakers containing 3,500 ml of Tris-buffered saline+0.5M Guanidine HCl. The beakers were placed in a 4° C. room on a magnetic stirrer overnight after which dialysis buffer was replaced with Tris-buffered saline+0.1M Guanidine HCl and dialysis continued for 12 hours. The buffer was then replaced with Tris-buffered saline+0.05M Guanidine HCl and dialysis continued overnight. The buffer was replaced with Tris-buffered saline (no guanidine), and dialysis continued for 12 hours. This was repeated three more times. The final leukotoxin solution was poured into a 2000 ml plastic roller bottle (Corning) and 13 ml of 100 mM PMSF (in ethanol) was added to inhibit protease activity. The solution was stored at −20° C. in 100 ml aliquots.

Purification of P. haemolytica Authentic 50K Outer Membrane Protein

Outer membrane preparations were electrophoresed on polyacrylamide gels after which the 50K outer membrane protein band was cut out as a single gel slice. Gel slices were crushed and suspended in 3 ml of a buffer consisting of 0.1% SDS, 0.05M Tris-HCl (pH 7.9), 0.1 mM EDTA, 5 mM dithiothreitol, 0.2M NaCl. This mixture was shaken for 2 hr at 37° C., after which the buffer without gel fragments was removed and dialyzed overnight against 1 liter of 10 mM ammonium bicarbonate. The dialyzed preparation was then lyophilized and the protein resuspended in phosphate-buffered saline prior to use.

Production of P. haemolytica Recombinant 50K Outer Membrane Protein

1. Cloning the 50K Protein Gene

The purified authentic 50K protein (50 ug) was mixed with Freund's incomplete adjuvant and injected intramuscularly into a New Zealand white rabbit. This immunization was repeated 14 days and 28 days later and the rabbit was bled 1 week after the last injection. The serum so derived contained high levels of antibodies against the 50K outer membrane protein. This antisera was used to immunologically screen a P. haemolytica gene library for recombinant clones expressing the 50K protein.

The lambda gt11 P. haemolytica gene library was constructed as described above for P. haemolytica leukotoxin. Plating of the library and the use of rabbit anti-50K antisera to select recombinant clones was done using established techniques (Maniatis, et al.; French et al. (1986) Anal. Biochem. 156:417–423). Plaques reacting with the anti-50K antisera were purified and propagated on E. coli strain Y1090 and transduced into E. coli strain Y1089 for high level expression of the 50K protein gene and subsequent purification of recombinant 50K B-galactosidase fusion protein.

2. Expression of the 50K Protein Gene

The recombinant 50K protein was expressed directly in E. coli Y1089 as a fusion product with B-galactosidase. E. coli Y1089 containing the recombinant lambda gt11 clone was grown at 32° C. until an $OD_{600}$ of 0.5 was reached. The culture was then shifted to 44° C. and grown for 20 min. Isopropyl-thiogalactopyranoside was then added to 10 mM (final concentration) and the culture was incubated at 37° C. for 1 hr. The cells were then harvested, broken by sonication, and the cell debris removed by centrifugation at 10,000×g for 15 min. The supernatant containing the 50K B-galactosidase fusion protein was then subjected to ammonium sulfate precipitation as described above (see "Purification of Recombinant Leukotoxin").

3. Purification of Recombinant 50K Protein

The recombinant 50K protein was purified using the same method used to purify recombinant leukotoxin with the exception that the affinity column consisted of p-aminophenyl-B-D-thiogalactopyranoside bound to agarose beads (purchased from Sigma). The dissolved pellet from the ammonium sulfate precipitation was applied to a 5 ml affinity column which was then washed with a buffer consisting of 10 mM Tris-HCl (pH 7.6), 250 mM NaCl, 10 mM $MgCl_2$, 1 mM EDTA and 0.1% Triton X-100 to remove unbound protein. The bound protein was subsequently eluted with 5 ml of 100 mM sodium borate (pH 10.0). The eluted protein was then dialysed overnight against 1 l of phosphate buffered saline prior to use.

Preparation of P. haemolytica Saline Extract For Use in Vaccination Trial A

A one liter culture of P. haemolytica A1 (strain B122) was prepared in Brain Heart Infusion Broth (Difco) and the cells were harvested by centrifugation at 9,000 rpm for 20 minutes with a Sorvall GSA rotor. The pellet was washed once with 200 ml of 0.85% sodium chloride (w/v) which had been preheated to 65° C. and and resuspended in 30 ml of the saline solution. The suspension was heated to 65° C. for 20 minutes with continuous stirring and the bacteria removed by centrifugation. The supernatant was decanted and stored at 4° C.

Preparation of P. haemolytica Saline Extract for Use in Vaccination Trial D

A saline extract was made as above with the following modifications. Cells were harvested by centrifugation at 5,000 rpm for 10 minutes with a Sorvall GS3 rotor. After washing, the pellet was resuspended in 100 ml of the sodium chloride solution which had been preheated to 65° C. The suspension was placed in a large flask (preheated to 65° C.), the bottom of which was covered with glass beads. The flask with cells was agitated vigorously in a New Brunswick G25 shaker (250–300 rpm) at 65° C. for one hour. The sample was then centrifuged for 20 minutes at 10,000 rpm in a Sorvall SS34 rotor. The supernatant was carefully decanted into a sterile bottle. Phenylmethyl sulfonylfluoride was added to a final concentration of 0.1 mM and stored at 20° C.

Preparation of the Vaccine Compositions

Each dose of vaccine compositions 1–4 and 6–9, listed in Table 1 above, were prepared by mixing 1.0 ml of the antigen listed (100 ug) 0.1M PBS, pH 7.2, with an equal volume of freshly prepared avridine. Groups of six calves were vaccinated intramuscularly and boosted three weeks later with the same vaccine composition. 10 days after boosting, the calves were exposed to bovine herpes virus-1 followed by exposure to P. haemolytica A-1 strain B122 four days later. Calves were monitored for clinical signs of disease, temperature and weight loss. The results of this trial (Vaccination Trial A) are shown in Table 2.

TABLE 2

Results of Vaccination Trial A of Example I

| Group | Antigen | Mortality (# of calves dead/6 calves) | Presence of Pasteurellosis Symptoms (+) | Mean Clinical Score per Day |
|---|---|---|---|---|
| 1 | Recombinant 50K Protein | 3 | + | 7.8 |
| 2 | Control (avridine only) | 5 | + | 10.7 |
| 3 | Authentic Leukotoxin | 1 | + | 4.0 |
| 4 | Recombinant Leukotoxin | 0 | − | 1.2 |

TABLE 2-continued

Results of Vaccination Trial A of Example I

| Group | Antigen | Mortality (# of calves dead/6 calves) | Presence of Pasteurellosis Symptoms (+) | Mean Clinical Score per Day |
|---|---|---|---|---|
| 5 | Recombinant 50K plus Authentic Leukotoxin | 1 | + | 2.6 |
| 6 | Recombinant 50K plus recombinant Leukotoxin | 3 | + | 6.3 |
| 7 | Saline Extract | 1 | + | 2.6 |
| 8 | Saline Extract plus Authentic Leukotoxin | 0 | – | 1.1 |

As illustrated in Table 2, groups 4 and 8 were completely protected while groups 3 and 5 were significantly protected. The control group, group 2, had the highest mortality rate. These results indicate that the recombinant leukotoxin:B-galactosidase fusion protein, as well as authentic leukotoxin, are effective immunogens for the prevention of bovine pneumonic pasteurellosis. Additionally, use of the 50K protein in combination with leukotoxin provided enhanced protection in comparison to the control group. It is possible that the protection afforded by the saline extract is at least partially due to the presence of leukotoxin.

A second vaccination trial (Vaccination Trial B) was carried out using the purified recombinant leukotoxin fusion protein described above. This protein was mixed with emulsigen (25% v/v) and calves vaccinated according to the groups listed in Table 3. The calves were boosted after 3 weeks and finally challenged with bovine herpes virus/P. haemolytica as described above. The results of this trial can be seen in Table 3.

TABLE 3

Results of Vaccination Trial B of Example 1

| Group | Mortality |
|---|---|
| 1. Emulsigen only | 8/9 |
| 2. Emulsigen + 100 ug antigen | 4/10 |
| 3. Emulsigen + 50 ug antigen | 4/6 |
| 4. Emulsigen + 25 ug antigen | 5/6 |
| 5. Emulsigen + 12.5 ug antigen | 5/6 |

As can be seen, Groups 2 and 3, administered emulsigen plus 100 ug and 50 ug of antigen, respectively, demonstrated a lower mortality rate than the control group. It should be noted that this experiment was done with a less than optimum adjuvant, possibly accounting for the higher mortality rates over those seen in vaccination trial A.

The immunogenicity of recombinantly produced LKT 352, prepared as described above, was tested in a third vaccination trial (Vaccination Trial C) as follows. Twelve beef-type calves were randomized into two groups of six. The control group was vaccinated with placebo comprised of sterile saline combined with adjuvant. The second group was vaccinated with 100 ug of LKT 352 in adjuvant. Two injections were given intramuscularly 21 days apart. Each calf was bled at the time of each vaccination and 12 days following the second vaccination. The anti-leukotoxin titers were determined by a standard ELISA and are shown in Table 4.

TABLE 4

Anti-Leukotoxin Titers of Calves Vaccinated with LKT 352

| Group | | Anti-Leukotoxin Titer at First Vaccination | Second Vaccination | 10 Days After Second Vaccination |
|---|---|---|---|---|
| Controls | 057 | 250 | 970 | 600 |
| | 065 | 3,500 | 10,000 | 20,000 |
| | 073 | 1,000 | 1,200 | 1,000 |
| | 081 | 230 | 200 | 230 |
| | 089 | 600 | 430 | 980 |
| | 097 | 500 | 500 | 500 |
| Mean | | 1,013 | 2,216 | 3,885 |
| LKT | 352 | 2,500 | 150,000 | 100,000 |
| | 070 | 600 | 4,000 | 14,000 |
| | 078 | 1,900 | 18,000 | 25,000 |
| | 086 | 250 | 15,000 | 120,000 |
| | 094 | 700 | 1,100 | 130,000 |
| | 102 | 170 | 800 | 35,000 |
| Mean | | 1,020 | 33,133 | 70,667 |

As can be seen, anti-leukotoxin titers were significantly higher in the LKT 352-treated group than the control calves at the time of the second vaccination and 10 days following the second vaccination.

The protective capacity of recombinantly produced LKT 352 combined with a saline extract of P. haemolytica was tested in a fourth vaccination trial (Vaccination Trial D). LKT 352 and P. haemolytica saline extract (SE) were prepared using the general methods outlined above. The saline extract was found to have a protein concentration of 250 ug/ml. It was diluted with sterile double distilled water to a final volume of 1330 ml in order to adjust the protein concentration to 150 ug/ml. The recombinant LKT 352 contained 250 ug/ml of protein. Polyacrylamide gel electrophoresis revealed the presence of one major band and therefore, this antigen was used with no further dilution. Each dose of vaccine contained 100 ug of the new leukotoxin and 50 ug of saline extract.

Calves were vaccinated twice intramuscularly, 21 days apart with one of the following:

(1) Placebo; or (2) P. haemolytica subunit vaccine (LKT 352 plus SE) in Emulsigen Plus; or (3) P. haemolytica subunit vaccine in Avridine.

The experimental schedule was as follows:

Day −31 1st vaccination

Day −10 2nd vaccination

Day 0 Challenge with BHV-1

Day 4 Challenge with P. haemolytica

Day 5 Clinical observation ends

The results of this study can be seen in Table 5. As can be seen, twenty-five percent of the control calves died. In contrast, there was no mortality in the two groups given the subunit vaccine. The morbidity was also significantly lower in the subunit vaccine groups than in the placebo group (Fisher Exact Test $p<0.05$).

TABLE 5

Results of Vaccination Trial D

| Vaccine Group | n = | % Morbidity[a] | % Mortality[b] | Mean[c] Clinical Score | Mean[c] Temp (°C.) | Mean[d] Sick Days | Mean Wt[e] Change (kg) |
|---|---|---|---|---|---|---|---|
| 1. Placebo | 8 | 100% | 25% | 1.04 | 40.3 | 4.5 | −3.6 |
| 2. LKT 352 + SE in Emulsigen Plus | 8 | 50%* | 0% | 0.36 | 39.4 | 1 | +2.25 |
| 3. LKT 352 + SE in Avridine | 8 | 50%* | 0% | 0.44 | 39.5 | 1 | +3.75 |

[a]% of calves that developed a fewer > 40.0 with clinical signs of BRD post *P. haemolytica* infection.
[b]% of calves that died of fibrinous pneumonia post *P. haemolytica* infection.
[c]Mean scores and temperatures of animals while alive.
[d]Mean days/calf that fever => 40.0 with clinical signs of BRD, calves that die are considered sick until end of trial.
[e]Mean change in weight (kg) from *P. haemolytica* infection until calf dies or trial ends.
*Morbidity was significantly lower (P < 0.05) than in the control group. Fisher's Exact Test.

A field trial (Vaccination Trial E) was carried out using the subunit vaccine comprised of LKT 352 and a *P. haemolytica* saline extract (SE). The vaccine formulations were as described in Vaccination Trial D.

The calves used were beef-type calves weighing from 250 kg to 325 kg. The calves were born during the spring, fall weaned, and purchased for the feedlot at auction markets. They were transported to the feedlot by truck and arrived within a few days of purchase.

Calves were randomly assigned to one of two vaccine groups. Calves in Group I were given a single 2 ml injection of the subunit *Pasteurella* vaccine intramuscularly. Calves in Group II were given a single 2 ml injection of placebo. The calves were processed at the time of arrival at the feedlot, and were assigned to one of the two treatment groups in rotation as they passed through a cattle chute. A technician administered the vaccines and recorded the treatment group to which each calf was assigned. A total of 2,324 calves were vaccinated, 1,168 in Group I and 1,156 in Group II.

Calves were kept and managed as typical feedlot animals. Feedlot cowboys were responsible for selecting and treating sick calves according to a protocol established by their consulting feedlot veterinarian. Selection of calves for treatment and post-mortem diagnosis was done without knowledge of the vaccination status of the calves. Records were maintained describing the daily diagnosis, temperature, and treatment of each sick calf. Calf health was monitored for 60 days after arrival. A gross post-mortem was done on all fatalities by a veterinarian within approximately 24 hrs of death and samples were submitted for further lab work if necessary. This information was used to establish morbidity (treatment) risks, and mortality risks. BRD morbidity risk scores were determined using the following equation:

$$\text{BRD Morbidity Risk} = \frac{\text{\# of calves sick with BRD in Group}}{\text{\# of calves in Group initially}}$$

The statistical significance of the differences between groups was established using risk ratios (or relative risk, RR), and by determining the 95% confidence intervals using the Taylor series confidence intervals when the comparison was between 2 groups. Risk ratios were established using the following equation:

$$\text{Risk Ratio (Relative Risk, } RR) = \frac{\text{Risk for One Group}}{\text{Risk for the Comparison Group}}$$

The significance of the differences was determined using the Mantel-Haenszel technique for summary risk ratios (MHRR) and the Greenland and Robins technique for calculating the 95% confidence intervals. All RRs were considered statistically significant if 95% confidence intervals did not include unity. When RRs and confidence intervals could not be calculated, the Fisher Exact 2-tailed test was used to determine the statistical significance between risks.

The results of this trial can be seen in Table 6. As is apparent, vaccination with LKT 352 in combination with a *P. haemolytica* saline extract (Group I) significantly reduced bovine respiratory disease morbidity and bovine respiratory disease mortality (all pneumonias) as compared to treatment with the placebo (Group II). The reduction in fibrinous pneumonia mortality was not significant at the 5% level. However, this is probably because a bovine herpesvirus-1 vaccine was also tested in combination with the *Pasteurella* vaccine. The BHV-1 vaccine appeared to cause immunosuppression which interfered with response to the *Pasteurella* vaccine.

TABLE 6

Protection From Natural Bovine Respiratory Disease (Vaccination Trial E)

| Group | BRD Morbidity | BRD Mortality | Fibrinous Pneumonia Mortality |
|---|---|---|---|
| I (Vaccine) | 259/1168 22.2%[a] | 6/1168 0.5%[a] | 5/1168 0.4% |
| II (Placebo) | 301/1156 26.0% | 16/1156 1.4% | 12/1156 1.0% |

[a]Significantly lower (P < 0.05) than Group II

Identification of Neutralizing Epitopes of Leukotoxin

The *P. haemolytica* leukotoxin protein contains a series of repeated amino acid domains near the carboxy terminus. These domains are likely to be epitopes useful in vaccine compositions. The consensus amino acid sequence is Gly-Gly-X-Gly-X-Asp, where X is Lys, Asp, Val or Asn. (Highlander et al. (1989) DNA 8:15–28.) However, other substitutions likely to render immunologically active peptides include substitutions with an aliphatic amino acid, such as Gly, Ala, Val, Leu, Ile, a charged amino acid such as Asp, Glu, Arg, His or Lys, or a corresponding neutral amino acid such as Asn or Gln.

Based on this information, a synthetic peptide of the sequence GGNGDDFIDGGKGNDLLHGG was constructed by standard solid phase technology on an Applied Biosystems peptide synthesizer. Mice were immumnized with authentic leukotoxins prepared from either *P.*

*haemolytica*, or Actinobacillus pleuropneumoniae (serotypes 1 and 5) at 100 micrograms per dose with Freund's Complete Adjuvant (first vaccination) or Freund's Incomplete Adjuvant (all subsequent vaccinations). High titer serum samples from immunized mice were tested, in a standard ELISA, for the following: (1) their ability to react with recombinant and authentic *P. haemolytica* leukotoxin; (2) their ability to react with the toxin produced by *A. pleuropneumoniae*; and (3) their ability to react with the synthetic peptide described above. The results, summarized in Table 7, are expressed as the relative reactivity at a serum dilution of 1 in 100,000.

TABLE 7

Presence of Synthetic Peptide Epitopes in Toxins from
*P. haemolytica* and *A. pleuropneumonia* serotypes 1 and 5

| | Relative Serological Response To: | | |
|---|---|---|---|
| Toxin Prepared From: | Synthetic Peptide | Actinobacillus Toxin | Pasteurella Toxin |
| *A. pleuropneumoniae* sero.5 | +++ | ++++ | ++ |
| *A. pleuropneumoniae* sero.1 | + | ++++ | + |
| *P. haemolytica* | +++ | not determined | ++++ |

This data indicated that animals vaccinated with either of the three leukotoxins developed antibodies which reacted with all toxins and a synthetic peptide based on a portion of the *P. haemolytica* toxin. Once an appropriate level of anti-peptide serum antibody was reached (ELISA titer of 100,000 or greater), spleen cells were fused with NS1 cells and monoclonal antibody-producing clones were isolated by standard techniques. Culture supernatants from these clones were tested for their ability to react with the synthetic peptide (above) and the respective toxins in an ELISA assay. The results for 2 clones are shown in Table 8.

TABLE 8

| | | Relative Reaction With: | | |
|---|---|---|---|---|
| Clone | Immunogen | Pasteurella Toxin | Synthetic Peptide | Actinobacillus Toxin |
| ET122-6A4-3 | Pasteurella toxin | ++++ | +++++ | ND[1] |
| N37-3F9-6 | Actinobacillus toxin | ND | ++++ | +++++ |

[1]Not determined

These results demonstrate that each of these monoclonal antibodies react with an epitope which is shared by the *P. haemolytica* and *A. pleuropneumoniae* toxins, and that this epitope is structurally similar to that of the synthetic peptide. This peptide is also structurally similar to a bovine rotavirus synthetic peptide of the sequence T M N G N E F Q T G G I G N L P I R N W N A C, representing amino acids 40–60 of the VP6 protein. the monoclonal antibodies described above can therefore be used to determine the degree of their cross-reactivity with rotavirus proteins based on the epitope represented by the synthetic peptides. furthermore, the immunologically active leukotoxin fragments might prove useful in immunizing agains rotavirus.

The antibodies above can also be tested for (1) their ability to react with and neutralize other similar toxins, including those produced by *E. coli, Proteus vulgaris, Proteus mirabilis* and *Actinobacillus actinomycetemcomitans*. A DNA sequence coding for this epitope can be cloned and expressed in either *E. coli, S. aureus* or Baculovirus.

EXAMPLE 2

*P. haemolytica* fimbriae were identified, purified and the protective capacity determined as described below.

1. Identification and Purification of Fimbriae

A crude shear fraction of *P. haemolytica* fimbriae was obtained in the following manner. *P. haemolytica* A1 strain B122 was grown on brain heart infusion agar for 13 hours at 37° C. in Nunc bioassay dishes (Gibco). The cells were then harvested using 20 ml phosphate buffered saline (PBS), pH 7.4, per plate and sheared by blending for 5 minutes in an Osterizer blender. Sheared cells were pelleted by centrifugation and the supernatant was examined by electron microscopy by placing samples on formvar-coated, carbon-stabilized copper grids. The samples were negatively stained with 1% uranyl acetate and examined with a Philips EM-410LS electron microscope operating at 60 kV. The structures obtained are shown in FIG. 6A and were referred to as "PH-K fimbriae." These structures were approximately 12 nm in diameter and varied in length to greater than 1000 nm.

SDS-polyacrylamide gel electrophoresis of this crude shear fraction was performed in a 12.5% (w/v) polyacrylamide gel (1.0 mm) with a Protean II vertical gel unit (Bio-Rad Laboratories, Richmond, Calif.). The SDS buffer system used was that described by the manufacturer. Several bands were present. A 35 kD protein was particularly abundant.

The crude shear fraction isolated above was further purified by centrifugation through a CsCl step gradient. Specifically, the crude shear fraction was centrifuged at 25,000 rpm overnight in a Beckman SW27 rotor. The pellet was dissolved in a small quantity of 10 mM Tris-HCl, pH 7.5 and applied to the top of a 1.0–1.5 g/ml CsCl gradient and centrifuged for 24–36 hours at 12° C. at 45,000 rpm in a Beckman 50Ti rotor. Two major bands were visible. Electron microscopy (as described above) of the lower band revealed largely membrane blebs while the upper band (density=1.32 g/ml) was composed of PH-K fimbriae as depicted in FIG. 6B.

Figure 6C:
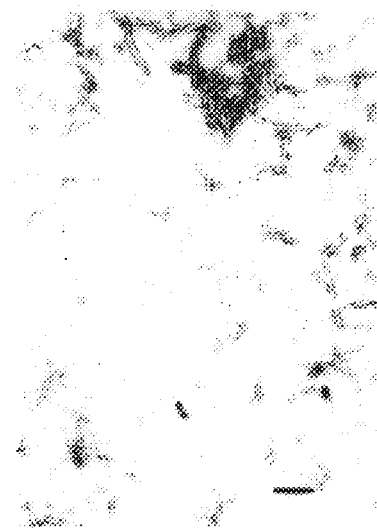

The fimbrial fraction was withdrawn and dialyzed overnight against 10 mM Tris-HCl, pH 7.5 and the centrifugation repeated. In some experiments, the fimbrial fraction was incubated in 5M urea at 37° C. for 5 hours prior to the second CsCl ultracentrifugation. Only one band at a density of 1.32 g/ml was observed. This fraction was further examined by polyacrylamide gel electrophoresis and electron microscopy as described above. This fraction appeared to contain pure PH-K fimbriae as depicted in FIG. 6C. The fimbriae were approximately 12 nm in diameter and varied in length to more than 500 nm. Only one band was present on SDS-PAGE gels, corresponding to a molecular weight of 35,000.

Monoclonal antibodies were raised against native fimbriae via the following method to test whether CsCl-purified fraction was indeed the PH-K subunit. BALB/c mice were immunized with 5 ug of purified fimbriae, boosted twice at approximately 2 weeks apart, and their spleens removed. Spleen cells were fused with NS-1 cells using the procedure described by Sabara et al. (1987) *J. Gen. Virol.* 68:123–133. Samples were screened by immunoblotting the purified fimbriae on SDS-PAGE gels as described by Sabara et al., supra. The monoclonal antibodies reacted only with the CsCl purified fraction on immunoblots, indicating that this represented the PH-K subunit.

Figure 7:
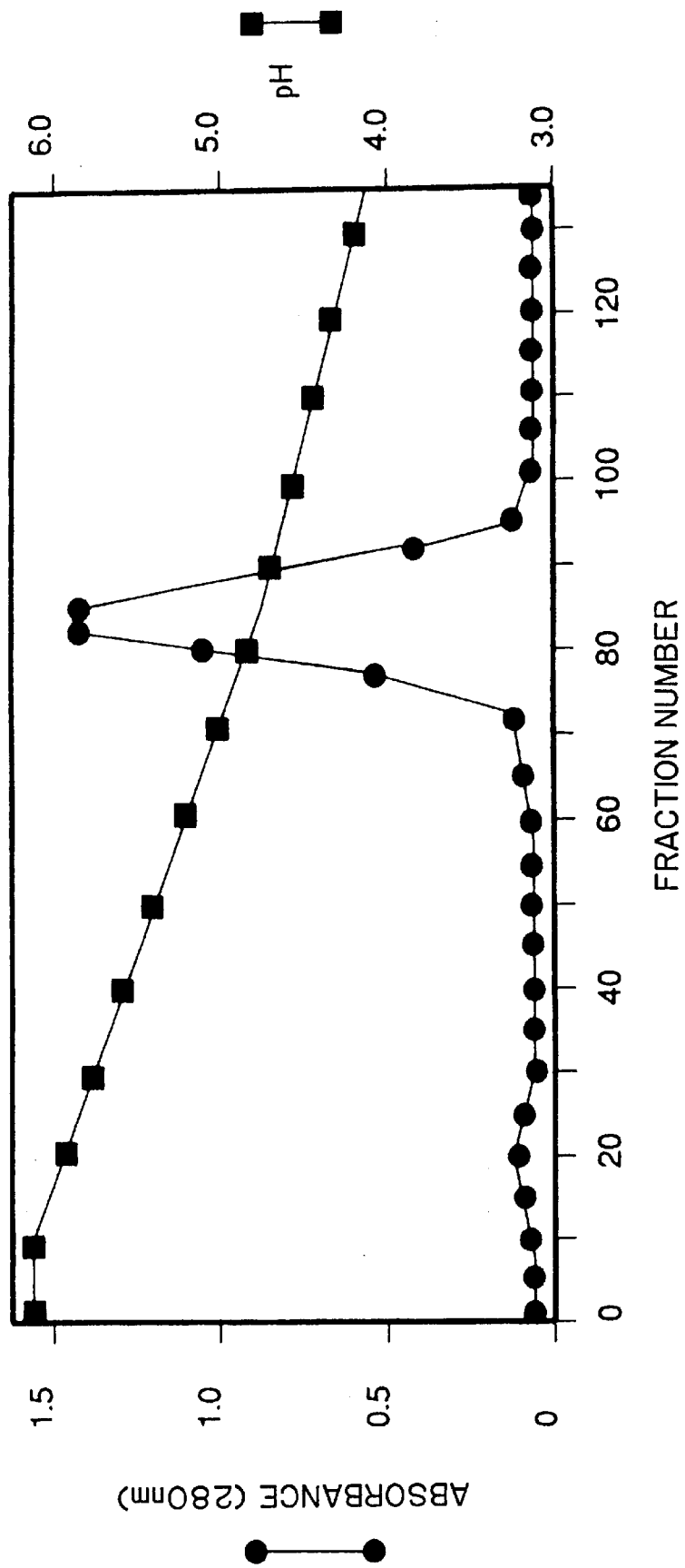
FIG. 7 depicts the chromatofocusing pattern of CsCl purified fimbriae.

To determine the isoelectric point of the purified fimbriae, the filaments were subjected to chromatography on a chromatofocusing column by the following method. A PBE 94 column (3×60 cm, Pharmacia Fine Chemicals, Uppsala, Sweden), was equilibrated with 25 mM histidine-HCl, pH 6.2. One hundred to five hundred ug of purified fimbriae were applied to the equilibrated column. The fimbriae were eluted with Polybuffer 74-HCl, pH 4.0 (Pharmacia) as described by the manufacturer. As illustrated in FIG. 7, one peak was eluted at pH 4.8. This pI value was confirmed by isoelectric focusing using a Phast Gel system (Pharmacia).

The hemagglutination properties of P. haemolytica whole cells, the crude shear fraction and the CsCl-purified fimbrial fraction were tested in the following manner. P. haemolytica A1 strain B122 was grown on brain heart infusion agar as described above. Cells were grown to a density of $10^{10}$ per ml and harvested in PBS. Serial dilutions were prepared. Bovine erythrocytes were washed three times with PBS and suspended at a concentration of 5% (v/v). 75 ul of the washed erythrocytes were added to equal volumes of diluted bacteria in microtiter plate wells (Costar, 96 well, Cambridge, Mass.). The plates were incubated for 24 hours at 37° C. and 14 hours at 4° C. The hemagglutination titer was the reciprocal of the highest dilution which exhibited a positive response.

Crude and purified fimbrial fractions were used in a hemagglutination assay as described above at a concentration of 1 mg/ml. Neutralization assays were conducted by preincubating the crude or purified fimbriae for 1 hour at room temperature with serum (1/50) from a calf which had survived a natural P. haemolytica infection. As illustrated in Table 9, antisera to P. haemolytica surface components was able to neutralize hemagglutination by whole cells and the crude shear fraction. However, CsCl-purified fimbriae exhibited no activity.

TABLE 9

Hemagglutination of Bovine Erythrocytes by
P. Haemolytica Strain b122

| Fraction | HA Titer |
| --- | --- |
| Cells | 64 |
| Cells plus antisera[a] | 2 |
| Crude shear fraction | 32 |
| Crude shear fraction plus antisera | 0 |
| Purified fimbriae | 0 |

[a]Antisera was from a calf which had recovered from a natural P. haemolytica infection.

The CsCl-purified fimbrial protein was sequenced using standard amino terminal sequencing techniques. The sequence was found to be 'xxxxxx-Ile-Ala-Ala-Leu-Asn-Thr-Leu-Asn-Arg-Leu-Ser-Ala-Asn-Asn-Gly-Ala-Ser-Gln-Lys-Asn- (Met or Phe).

Production of P. haemolytica Recombinant Fimbrial Protein

A nucleic acid probe based on the amino-terminal protein sequence disclosed above can be prepared. The sequence of the synthetic probe is sequence of the synthetic probe is 5'-CAA/GAAA/GAATATGGAA/GAAA/GTT-3'. The probe can be labeled with $^{32}$p and hybridized to Southern blotted P. haemolytica genomic DNA digested with various restriction endonucleases. The fragment can be cloned into the vector lambda-ZAP and identified by colony hybridization with the above oligonucleotide probe. The cloned DNA containing the area of hybridization can be sequenced in order to confirm that it codes for the same amino acid sequence as determined above. Subclones can be constructed and the entire gene sequenced. The fimbrial protein gene can be expressed in any suitable expression system known in the art.

2. Vaccine Compositions Made from Purified Fimbriae

Figure 8:
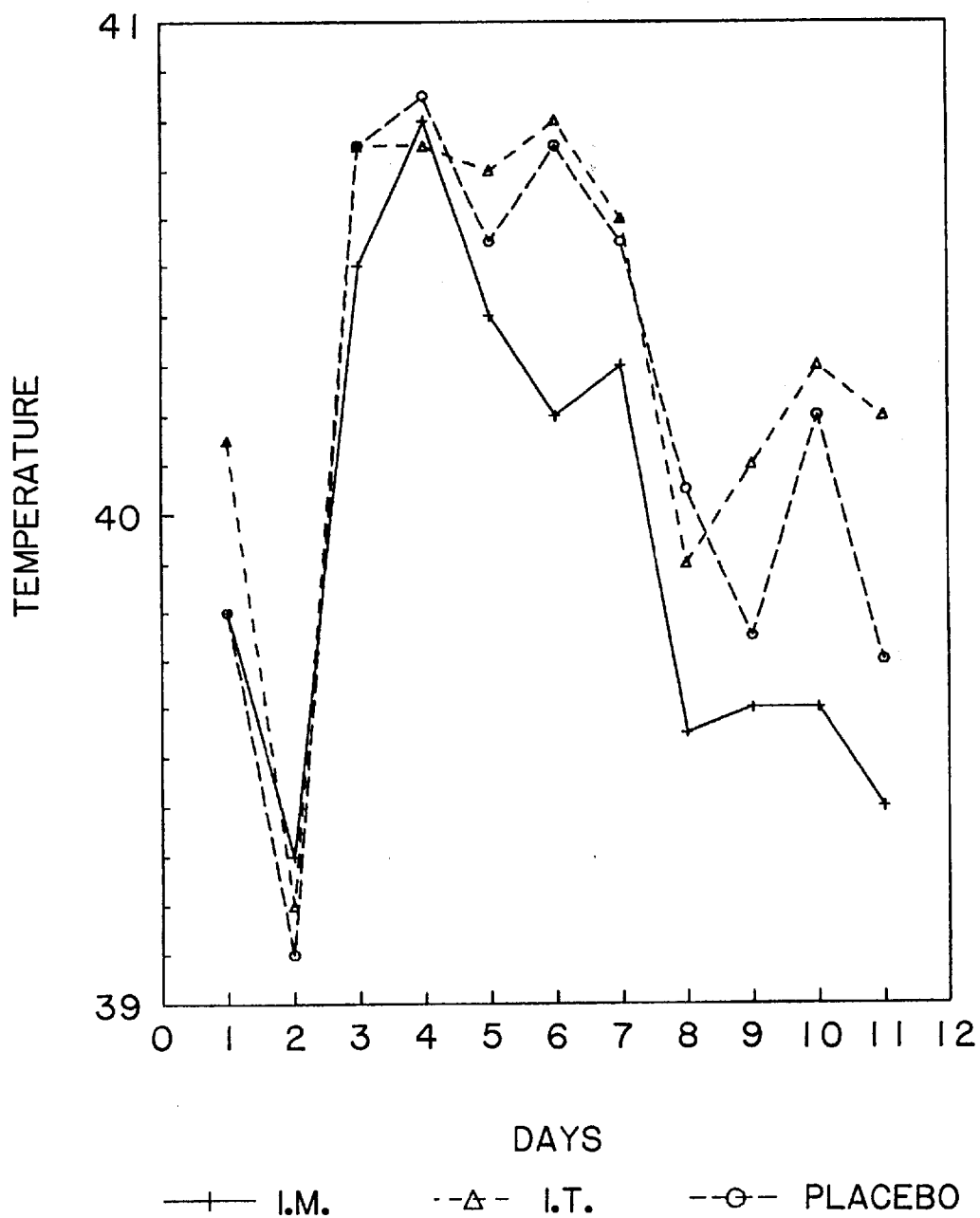
FIG. 8 shows the temperature response in calves challenged with bovine herpes virus-i and *P. haemolytica* after vaccination with *P. haemolytica* fimbriae as described in Example II, vaccination trial 1.
Figure 9:
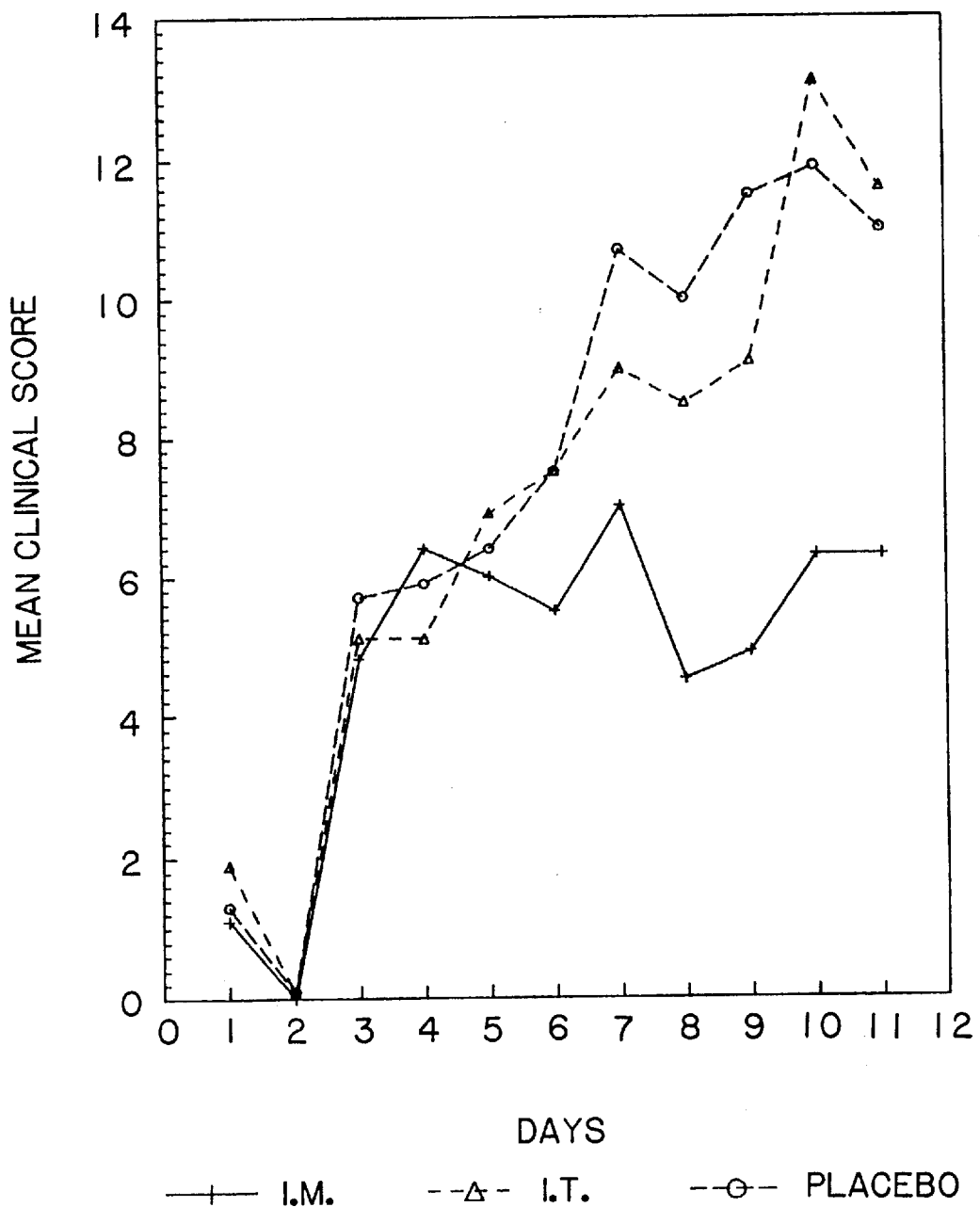
FIG. 9 summarizes the clinical scores obtained in Example II, vaccination trial 1.
Figure 10:
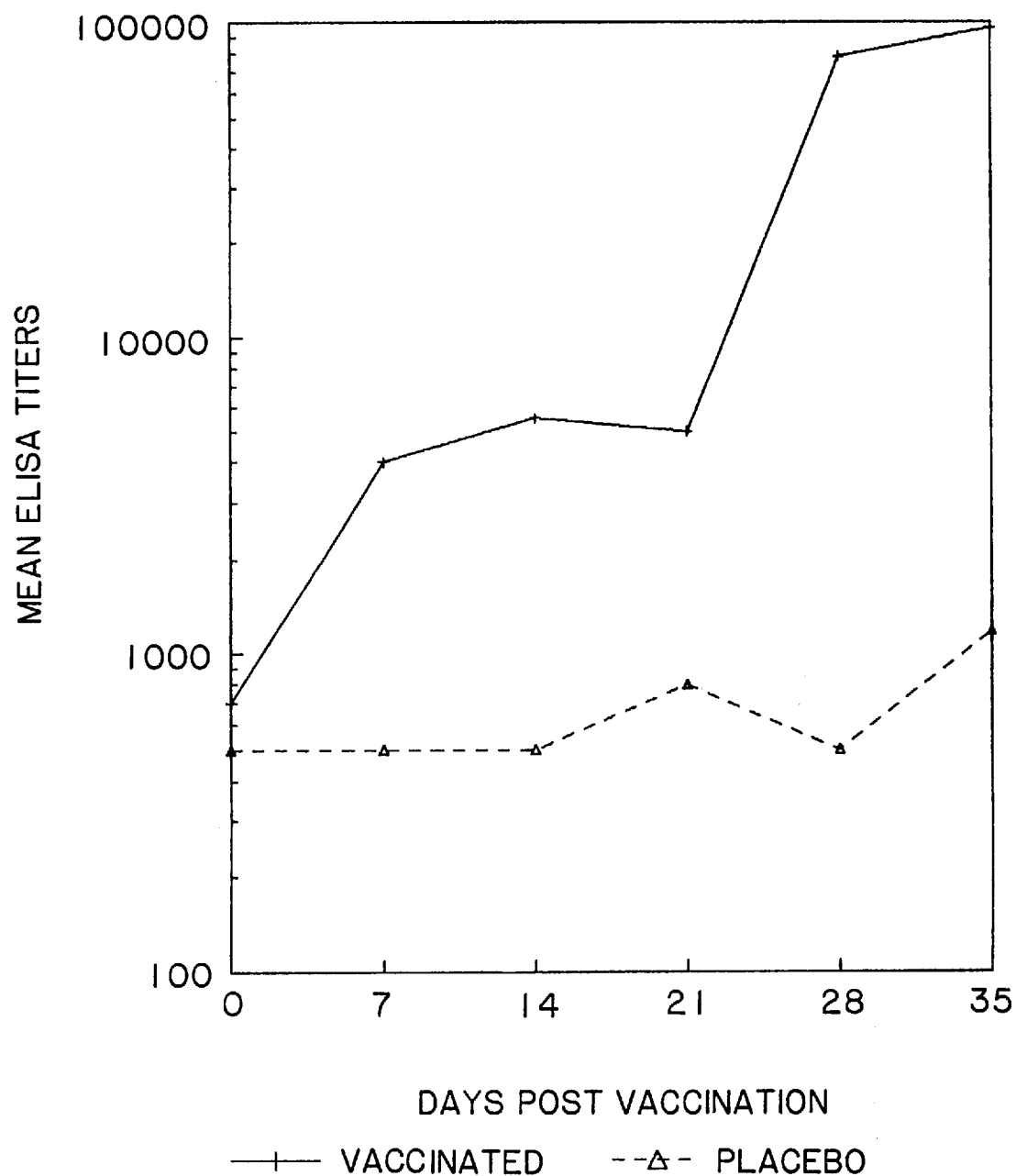
FIG. 10 shows the mean ELISA titers obtained in Example II, vaccination trial 2.
Figure 11:
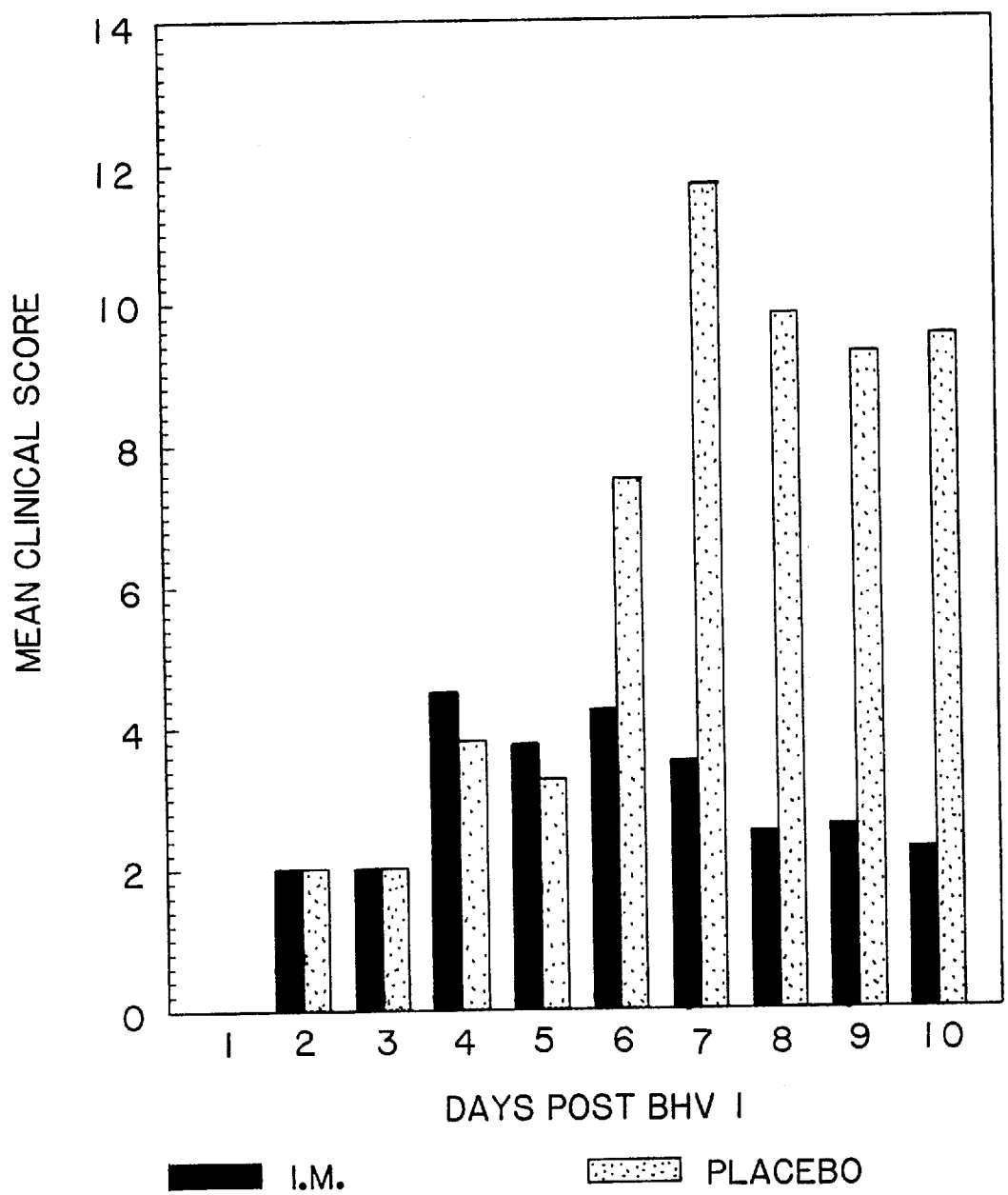
FIG. 11 depicts the mean clinical scores obtained in Example II, vaccination trial 2.
Figure 12:
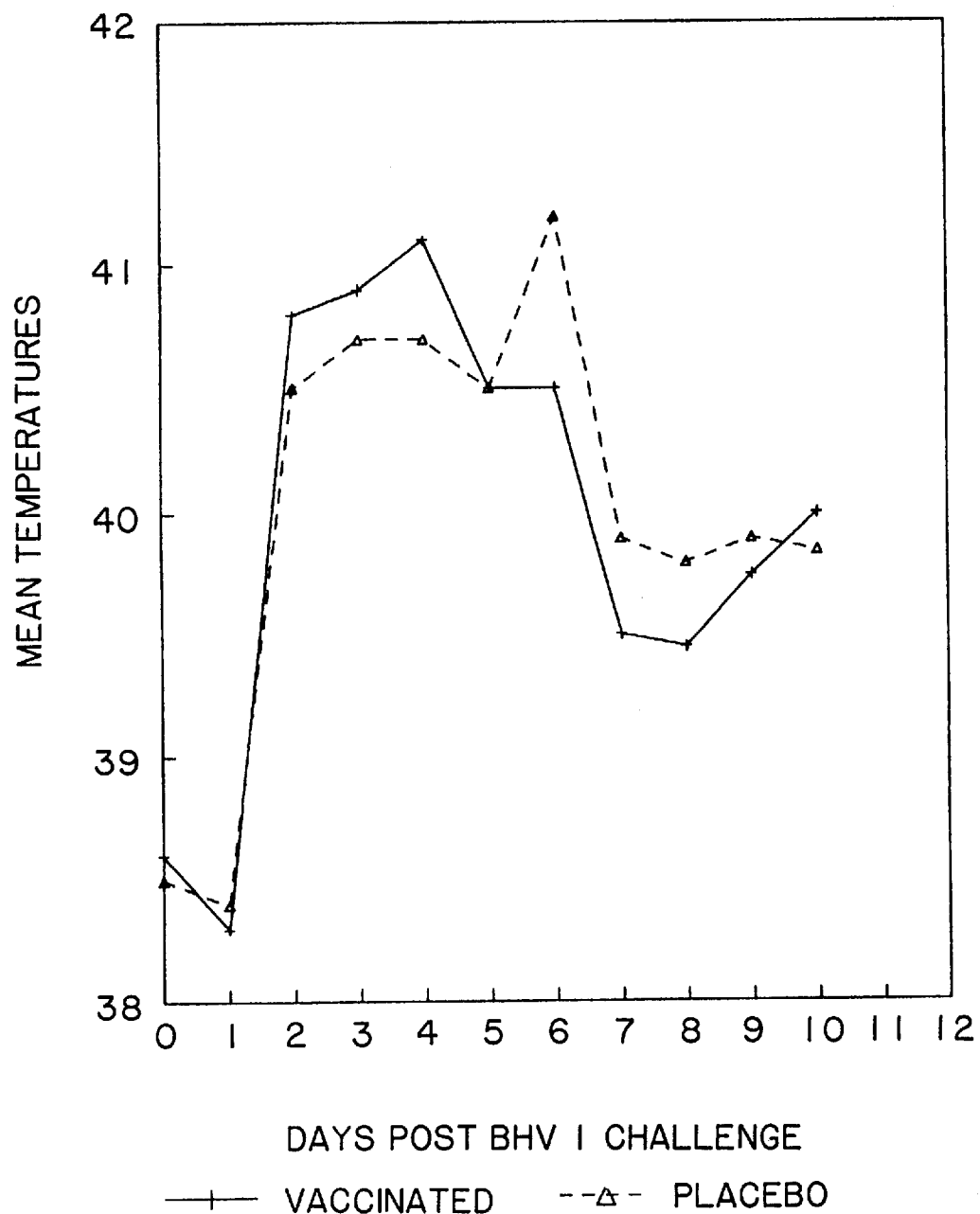
FIG. 12 shows the temperature response in calves from Example II, vaccination trial 2.
Figure 13:
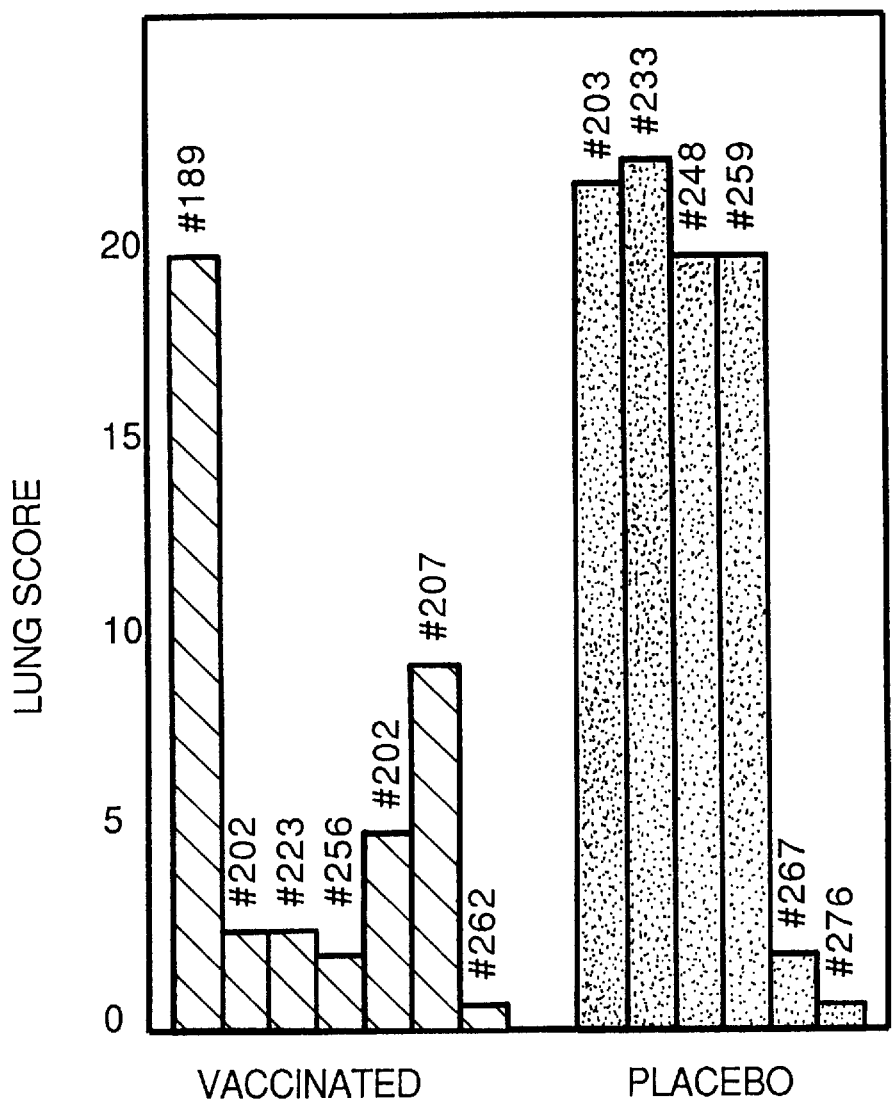
FIG. 13 depicts the lung scores obtained in calves from Example II, vaccination trial 2.

In a first trial, vaccines were made by mixing 100 ug in 1.0 ml of 0.1M PBS, pH 7.2, of the CsCl-purified fimbriae with 1.0 ml of avridine. Six calves were injected intramuscularly (I.M.) with the vaccine composition, six calves were injected intratracheally (I.T.), and a third group of six calves was injected I.M. with a control substance which contained avridine but no fimbrial protein. The animals were boosted 24 days later. Ten days after boosting, the animals were challenged with Bovine herpes virus-1, followed four days later by exposure to P. haemolytica A1 strain B122. The calves were checked daily for clinical signs of pneumonia, temperature and feeding. In addition, weight loss and lung scores were recorded at necropsy. The results are summarized in Tables 10–12 below and FIGS. 8 and 9.

TABLE 10

Mean ELISA Titers (Vaccine Trial #1) of Calves
Immunized with P. haemolytica PH-K Fimbria

| | MEAN TITER | | | |
| --- | --- | --- | --- | --- |
| GROUP | DAY 0 | DAY 14 | DAY 21 | DAY 32 |
| VACCINATED I.M. | 2,650 | 18,000 | 15,600 | 58,200 |
| VACCINATED I.T. | 1,433 | 3,667 | 4,783 | 10,500 |
| CONTROL | 425 | 1,208 | 5,267 | 8,267 |

I.M. = vaccinated intramuscularly
I.T. = vaccinated intratracheally
Control = Avridine

TABLE 11

P. haemolytica Pili Vaccine Experiment: Clinical Scores
(Vaccine Trial #1)

| Calf ID | Treatment | Cumulative Clinical Score | Total Sick Days | Outcome | Lung Score |
| --- | --- | --- | --- | --- | --- |
| 276 | Phaem Fimbriae (100 ug IM) | 32 | 0 | Survived | 0 |
| 277 | Phaem Fimbriae (100 ug IM) | 45 | 0 | Survived | 0 |
| 278 | Phaem Fimbriae (100 ug IM) | 43 | 0 | Survived | 0 |
| 279 | Phaem Fimbriae (100 ug IM) | 102 | 4 | Died | 26 |
| 280 | Phaem Fimbriae (100 ug IM) | 45 | 0 | Survived | 0 |
| | Mean | 53.4 | 4 | 4/5 Survived | mean = 5.2 median = 0 |

TABLE 11-continued

*P. haemolytica* Pili Vaccine Experiment: Clinical Scores
(Vaccine Trial #1)

| Calf ID | Treatment | Cumulative Clinical Score | Total Sick Days | Outcome | Lung Score |
|---|---|---|---|---|---|
| 282 | Phaem Fimbriae (100 ug IT) | 42 | 0 | Survived | 0 |
| 283 | Phaem Fimbriae (100 ug IT) | 61 | 2 | Survived | 0 |
| 284 | Phaem Fimbriae (100 ug IT) | 97 | 4 | Died | 19 |
| 285 | Phaem Fimbriae (100 ug IT) | 122 | 4 | Died | 18 |
| 286 | Phaem Fimbriae (100 ug IT) | 57 | 0 | Survived | 0 |
| 287 | Phaem Fimbriae (100 ug IT) | 55 | 0 | Survived | 0 |
| | Mean | 78.4 | 10 | 4/5 Survived | mean = 6.2 median = 0 |
| 288 | Control (Avridine) | 40 | 0 | Survived | 0 |
| 289 | Control (Avridine) | 56 | 1 | Survived | 0 |
| 290 | Control (Avridine) | 113 | 5 | Died | 11 |
| 291 | Control (Avridine) | 63 | 1 | Survived | 0 |
| 292 | Control (Avridine) | 49 | 0 | Survived | 0 |
| 293 | Control (Avridine) | 133 | 6 | Died | 14 |
| | Mean | 82.8 | 13 | 4/6 Survived | mean = 4.2 median = 0 |

TABLE 12

*P. haemolytica* Vaccine Experiment: Weight Changes
(Vaccine Trial #1)

| Calf ID | Treatment | Initial Weight (kg) | Final Weight (kq) | Weight Change |
|---|---|---|---|---|
| 276 | Phaem fimbriae Intramuscular | 170 | 176 | 6 |
| 277 | Phaem fimbriae Intramuscular | 168 | 158 | −10 |
| 278 | Phaem fimbriae Intramuscular | 156 | 147 | −9 |
| 279 | Phaem fimbriae Intramuscular | 185 | 172 | −13 |
| 280 | Phaem fimbriae Intramuscular | 190 | 185 | −5 |
| 281 | Phaem fimbriae Intramuscular | Excluded from study | | |
| | | | | Mean −6.2 |
| 282 | Phaem fimbriae Intratracheal | 166 | 169 | 3 |
| 283 | Phaem fimbriae Intratracheal | 174 | 162 | −12 |
| 284 | Phaem fimbriae Intratracheal | 208 | 186 | −22 |
| 285 | Phaem fimbriae Intratracheal | 195 | 192 | −3 |
| 286 | Phaem fimbriae Intratracheal | 183 | 169 | −14 |
| 287 | Phaem fimbriae Intratracheal | 172 | 167 | −5 |
| | | | | Mean −8.8 |
| 288 | Avridine Control | 230 | 228 | −2 |
| 289 | Avridine Control | 168 | 158 | −10 |
| 290 | Avridine Control | 155 | 156 | 1 |
| 291 | Avridine Control | 225 | 209 | −16 |
| 292 | Avridine Control | 196 | 195 | −1 |
| 293 | Avridine Control | 183 | 170 | −13 |
| | | | | Mean −6.8 |

As can be seen, serum antibody titers were lowest in the control group and highest in the group which received the fimbriae vaccine I.M. Calves vaccinated I.T. did not have significantly higher titers than the control group. The clinical signs of pneumonia and number of sick days was lower in the I.M. fimbriae vaccinated group than in the control group.

A second vaccine trial was carried out. One group of 7 calves was administered the vaccine composition I.M. as described above containing the purified fimbrial protein. A second group of six calves received a control composition containing avridine only. The calves were boosted 22 days later and challenged with bovine herpes virus-1 15 days after being boosted. The calves were then exposed to *P. haemolytica* 4 days later. The results are summarized in FIGS. 10–13. The fimbrial-vaccinated group was clearly protected against experimental challenge with *P. haemolytica* as reflected in lower mortality, clinical scores and lung scores. Only one calf in the vaccinated group had a significant lung score.

Thus *P. haemolytica* purified fimbrial protein shows utility in a vaccine against shipping fever. Vaccination may reduce colonization of the lung resulting in decreased morbidity and mortality. It is likely that a subunit vaccine derived from the recombinant fimbrial protein will also be useful for this purpose.

EXAMPLE 3

Plasmin receptors on the outer membrane of *P. haemolytica* A1 strain B122 were identified by running fibrin plate assays since plasmin has the ability to lyse fibrin. Fibrin plates were prepared by clotting 10 ml of 0.1% bovine fibrinogen (Sigma) in phosphate-buffered saline, pH 7.2, with 0.2 ml of bovine thrombin (10 NIH U/ml) in 0.5M $CaCl_2$. Bacteria were prepared by growing *P. haemolytica* A1 strain B122 overnight at 37° C. in brain heart infusion agar, performing a 100-fold dilution and growing the diluted culture until it reached log-phase (approximately 6 hours). The bacteria were then washed once and 0.2 g (weight/volume) of the washed cells were incubated with 50 picomoles of bovine plasmin in 2 ml of VBS-gel (Veronal-buffered saline, pH 7.35 containing 1.0 mM $MgCl_2$, 0.15 mM $CaCl_2$ and 0.1% gelatin). The reaction was allowed to proceed for 45 minutes at 37° C. after which the mixture was centrifuged at 2500 rpm for 15 minutes with two washes in VBS-gel. The washed cell pellet was resuspended in 400 microliters VBS-gel and 50 microtiter samples were spotted on the fibrin plates prepared above. A control of free plasmin was included. The reaction proceeded overnight in a moist chamber at 37° C. The fibrin clot was clearly hydrolyzed by log-phase bacteria. The degree of hydrolysis of the fibrin clot was scored by measuring the area of the zone of clearing from the under-side of the plate.

The above experiment was repeated with cells in log-phase as well as with cells in stationary-phase. No clot hydrolysis was observed with the stationary-phase cells indicating that the plasmin receptor is expressed only by actively growing cells.

Plasmin is able to degrade a large number of substrates, including casein. Therefore, the above experiment was repeated using skim milk-agarose plates and log-phase bacterial cultures. Lysis was visible after incubation at 37° C., however not to the same degree as observed with the fibrin medium.

To test the ability of *P. haemolytica* serotypes 1–11 to bind plasmin, these serotypes were tested using skim milk-agarose plates as described above. All serotypes were able to degrade this substrate, although the results varied widely. The results can be seen in Table 13.

TABLE 13

Plasmin-Binding Capacity of Different *P. haemolytica* Serotypes

| Strain[1] | Serotype | Plasmin-binding[2] |
|---|---|---|
| PH45 | 1 | +++ |
| PH46 | 1 | ++ |
| PH47 | 2 | ++/− |
| PH48 | 3 | +/− |
| PH49 | 4 | ++ |
| PH50 | 6 | +++ |
| PH51 | 7 | ++ |
| PH52 | 8 | ++++ |
| PH53 | 9 | ++/− |
| PH54 | 5 | ++++/− |
| PH55 | 10 | + |
| PH56 | 11 | ++++ |

[1]Strain PH45 is the same as B122 and is from the VIDO culture collection. All others were obtained from the American Type Culture Collection.
[2]Plasmin-binding was scored by the relative amounts of lysis of skim milk.

Figure 14:
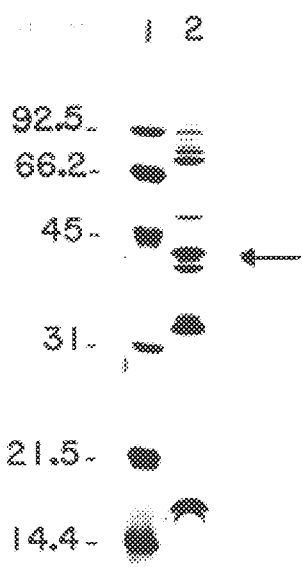
FIG. 14 shows the outer membrane profile of *P. haemolytica* A1. The arrow indicates the position of the plasmin receptor protein.

The receptor protein was identified by separating outer membrane proteins from a serotype 1 isolate of *P. haemolytica* on an SDS-polyacrylamide gel. The components were electroblotted to a nitrocellulose membrane and reacted with biotinylated plasmin 50–200 ng/ml (Sigma). Strepavidin-alkaline phosphatase was added to the membrane and the membrane stained using nitroblue tetrazolium and bromo-chloro-indolyl phosphate. One band corresponding to an approximate molecular weight of 41,000 was visible. This corresponds to a minor outer membrane component (see FIG. 14).

Plasminogen is the inactive zymogen precursor of plasmin. To test whether *P. haemolytica* was able to bind plasminogen, the above experiment was repeated using biotinylated plasminogen. Identical results were obtained indicating that this bacterium has the ability to bind both plasmin and plasminogen.

Production of *P. haemolytica* Recombinant Plasmin Receptor

A *P. haemolytica* A1 gene library was constructed in *E. coli* using the cosmid vector pHC79. The library was screened for clones able to bind biotinylated bovine plasmin. The resulting positive clones were tested for their ability to bind plasmin and subsequently degrade a fibrin clot. Positive recombinants can be subcloned and the coding region sequenced. The plasmin receptor gene can be expressed in *E. coli*, baculovirus and other expression systems known in the art.

The plasmin/plasminogen receptor of *P. haemolytica* may function as a virulence determinant by permitting rapid penetration of the organism in the lower respiratory tract. Thus, immunization with this protein may result in protective immunity by blocking subsequent colonization of the lung. Additionally, monospecific antisera or the cloned gene may be useful in diagnostic tests for *P. haemolytica*.

Thus, *P. haemolytica* purified and recombinant proteins for use in stimulating immunity against pneumonia and other respiratory diseases have been disclosed. Although preferred embodiments of the subject invention have been described in some detail, it is understood that obvious variations can be made without departing from the spirit and the scope of the invention as defined by the appended claims.

We claim:

1. A vaccine composition capable of eliciting an immunological response in a subject to which it is administered, said composition comprising:

(a) an immunogenic *Pasteurella haemolytica* leukotoxin polypeptide, wherein said leukotoxin polypeptide has a truncation selected from the group consisting of an N-terminal truncation, a C-terminal truncation, and an N-terminal and a C-terminal truncation, and further wherein said leukotoxin polypeptide comprises the amino acid sequence encoded by the leukotoxin gene present in plasmid pAA342; and (b) a pharmaceutically acceptable vehicle.

2. The vaccine composition of claim 1, wherein said immunogenic leukotoxin is LKT 352 as depicted in FIGS. 5A–5F.

3. The vaccine composition of claim 1, wherein said immunogenic leukotoxin is the truncated leukotoxin encoded by clone pAA342.

4. The vaccine composition of claim 1, wherein said immunogenic leukotoxin is the truncated leukotoxin encoded by clone pAA101.

5. The vaccine composition of claim 1 wherein the composition further comprises a saline extract of *P. haemolytica*.

6. The vaccine composition of claim 1 further comprising an adjuvant.

7. The vaccine composition of claim 5 further comprising an adjuvant.

8. The vaccine composition of claim 2 further comprising an adjuvant.

9. The vaccine composition of claim 3 further comprising an adjuvant.

10. The vaccine composition of claim 4 further comprising an adjuvant.

11. A method of preventing or ameliorating respiratory disease in a ruminant subject, said method comprising administering an effective amount of a vaccine composition according to claim 1 to said ruminant subject.

12. A method for preventing or ameliorating respiratory disease in a ruminant subject, said method comprising administering an effective amount of a vaccine composition according to claim 5 to said ruminant subject.

13. A method of preventing or ameliorating respiratory disease in a ruminant subject, said method comprising administering an effective amount of a vaccine composition according to claim 6 to said ruminant subject.

14. A method of preventing or ameliorating respiratory disease in a ruminant subject, said method comprising administering an effective amount of a vaccine composition according to claim 7 to said ruminant subject.

15. A method of preventing or ameliorating respiratory disease in a ruminant subject, said method comprising administering an effective amount of a vaccine composition according to claim 2 to said ruminant subject.

16. A method of preventing or ameliorating respiratory disease in a ruminant subject, said method comprising administering an effective amount of a vaccine composition according to claim 3 to said ruminant subject.

17. A method of preventing or ameliorating respiratory disease in a ruminant subject, said method comprising administering an effective amount of a vaccine composition according to claim 4 to said ruminant subject.

18. A method of preventing or ameliorating respiratory disease in a ruminant subject, said method comprising administering an effective amount of a vaccine composition according to claim 8 to said ruminant subject.

19. A method of preventing or ameliorating respiratory disease in a ruminant subject, said method comprising administering an effective amount of a vaccine composition according to claim 9 to said ruminant subject.

20. A method of preventing or ameliorating respiratory disease in a ruminant subject, said method comprising administering an effective amount of a vaccine composition according to claim 10 to said ruminant subject.

\* \* \* \* \*